(12) United States Patent
Blasi et al.

(10) Patent No.: US 7,737,256 B2
(45) Date of Patent: Jun. 15, 2010

(54) ANTIBODY AGAINST UPA/UPAR

(75) Inventors: Francesco Blasi, Milan (IT); Nicolai Sidenius, Milan (IT); Massimo Resnati, Milan (IT); Anna Mondino, Milan (IT); Guido Poli, Milan (IT); Massimo Alfano, Milan (IT)

(73) Assignee: Fondazione Centro San Raffaele Del Monte Tabor, Milan (IT)

( * ) Notice: Subject to any disclaimer, the term of this patent is extended or adjusted under 35 U.S.C. 154(b) by 1483 days.

(21) Appl. No.: 10/470,245

(22) PCT Filed: Jan. 22, 2002

(86) PCT No.: PCT/EP02/00603

§ 371 (c)(1),
(2), (4) Date: Jan. 29, 2004

(87) PCT Pub. No.: WO02/058714

PCT Pub. Date: Aug. 1, 2002

(65) Prior Publication Data

US 2004/0115190 A1 Jun. 17, 2004

Related U.S. Application Data

(60) Provisional application No. 60/263,198, filed on Jan. 25, 2001.

(51) Int. Cl.
*C07K 16/00* (2006.01)
(52) U.S. Cl. .................................. 530/387.1
(58) Field of Classification Search ........................ None
See application file for complete search history.

(56) References Cited

U.S. PATENT DOCUMENTS 6,077,508 A 6/2000 Rabbani et al.
6,462,170 B1 * 10/2002 Blasi et al. .................. 530/300

FOREIGN PATENT DOCUMENTS

EP 0 691 350 A 1/1996
WO WO 90 12091 * 11/1990
WO WO 96 13160 A 5/1996
WO WO 01 38871 A 5/2001

OTHER PUBLICATIONS

Andreasen Peter A. et al., "The urokinase-type plasminogen activator system in cancer metastasis: A review", International Journal of Cancer, 1997, vol. 72, No. 1, pp. 1-22, XP-002210773.
Del Rosso M. et al., "The urokinase-type plasminogen activator system and inflammatory joint diseases", Clinical and Experimental Rheumatology, Italy, 1999, vol. 17, No. 4, pp. 485-498, XP-001096329.
Fazioli Francesca et al., "A urokinase-sensitive region of the human urokinase receptor is responsible for its chemotactic activity", European Molecular Biology Organization Journal (EMBO), 1997, vol. 16, No. 24, pp. 7279-7286, XP-002072480.
Sidenius Nicolai et al., "Serum level of soluble urokinase-type plasminogen activator receptor is a strong and independent predictor of survival in human immunodeficiency virus infection", Blood, W.B. Saunders Company, Orlando, FL, US, 2000, vol. 96, No. 13, pp. 4091-4095, XP-002166383.
Sidenius Nicolai et al., "Shedding and cleavage of the urokinase receptor (uPAR); Identification and characterisation of uPAR fragments in vitro and in vivo", FEBS Letters, 2000, vol. 475, No. 1, pp. 52-56, XP-004337232.
Slot Ole et al., "Soluble urokinase plasminogen activator receptor in plasma of patients with inflammatory rheumatic disorders: Increased concentrations in rheumatoid arthritis", Annals of the Rheumatic Diseases, 1999, vol. 58, No. 8, pp. 488-492, XP-001097411.
Wada Manabu et al., "Amino-terminal fragment of urokinase-type plasminogen activator inhibits HIV-1 replication", Biochemical and Biophysical Research Communications, Academic Press, San Diego, CA, US, 2001, vol. 284, No. 2, pp. 346-351, XP-002183644.

* cited by examiner

*Primary Examiner*—Michael Pak
(74) *Attorney, Agent, or Firm*—Rothwell, Figg, Ernst & Manbeck, P.C.

(57) ABSTRACT

The invention herein disclosed relates to the anti-HIV action of uPAR-activators or activated uPAR molecules, the control of chemotaxis and cell migration by agents interfering with uPAR activation, a method for determining activated uPAR forms, the use of agents interfering with uPA/uPAR interaction for the diagnosis or therapy of diseases.

2 Claims, 17 Drawing Sheets

|  | Untreated | PMA | PMA+proUPA |
|---|---|---|---|
| Nil | 81 ± 18 | 6772 ± 135 | 2953 ± 275 |
| R5 | 109 ± 4 | 6614 ± 1271 | 7303 ± 98 |
| R3 | 87 ± 16 | 6749 ± 876 | 7404 ± 998 |
| R4 | 88 ± 3 | 6284 ± 868 | 3446 ± 755 |
| Isotype Ctrl (aTNP) | 86 ± 33 | 6451 ± 135 | 3692 ± 505 |

Figure 3

|  | U937 cSB (+) | U937 c10 (+) | U937 c12 (-) | U937 c34 (-) |
|---|---|---|---|---|
| HIV-1 Replication | +++ | +++ | +/- | +/- |
| UPAR (ng/mg) Untreated cells | 1.6 +/- 0.1 | 1.4 +/- 0.1 | 14.4 +/- 0.1 | 16.3 +/- 0.1 |
| UPAR (ng/mg) PMA-treated | 2.2 +/- 0.1 | 2.6 +/- 0.3 | 71.1 +/- 0.1 | 117 +/- 0.7 |

Figure 8A

| CHEMOTAXIS (% of CONTROL) | | |
|---|---|---|
| | No Addition | Anti-FPRL1/LXA4R Ab |
| None | 100 | 100 |
| 10 nM ATF | 167 | 100 |
| 2 nM MCP-1 | 257 | 203 |

Figure 14

```
                         SEQUENCE LISTING

<160> NUMBER OF SEQ ID NOS: 14

<210> SEQ ID NO 1
<211> LENGTH: 12
<212> TYPE: PRT
<213> ORGANISM: Homo sapiens

<400> SEQUENCE: 1

Ala Val Thr Tyr Ser Arg Ser Arg Tyr Leu Glu Cys
1               5                   10

<210> SEQ ID NO 2
<211> LENGTH: 5
<212> TYPE: PRT
<213> ORGANISM: Homo sapiens

<400> SEQUENCE: 2

Ser Arg Ser Arg Tyr
1               5

<210> SEQ ID NO 3
<211> LENGTH: 8
<212> TYPE: PRT
<213> ORGANISM: Homo sapiens

<400> SEQUENCE: 3

Ser Arg Ser Arg Tyr Leu Glu Cys
1               5

<210> SEQ ID NO 4
<211> LENGTH: 12
<212> TYPE: PRT
<213> ORGANISM: Homo sapiens

<400> SEQUENCE: 4

Ala Ser Trp Gly Gly Thr Pro Glu Glu Arg Leu Lys
1               5                   10

<210> SEQ ID NO 5
<211> LENGTH: 11
<212> TYPE: PRT
<213> ORGANISM: Homo sapiens

<400> SEQUENCE: 5

Val Thr Tyr Ser Arg Ser Arg Tyr Leu Glu Cys
1               5                   10
```

```
<210> SEQ ID NO 6
<211> LENGTH: 10
<212> TYPE: PRT
<213> ORGANISM: Homo sapiens

<400> SEQUENCE: 6

Thr Tyr Ser Arg Ser Arg Tyr Leu Glu Cys
1               5                   10

<210> SEQ ID NO 7
<211> LENGTH: 9
<212> TYPE: PRT
<213> ORGANISM: Homo sapiens

<400> SEQUENCE: 7

Tyr Ser Arg Ser Arg Tyr Leu Glu Cys
1               5

<210> SEQ ID NO 8
<211> LENGTH: 14
<212> TYPE: PRT
<213> ORGANISM: Homo sapiens

<400> SEQUENCE: 8

Gly Arg Ala Val Thr Tyr Ser Arg Ser Arg Tyr Leu Glu Cys
1               5                   10

<210> SEQ ID NO 9
<211> LENGTH: 196
<212> TYPE: PRT
<213> ORGANISM: Homo sapiens

<400> SEQUENCE: 9

Ala Val Thr Tyr Ser Arg Ser Arg Tyr Leu Glu Cys Ile Ser Cys Gly
1               5                   10                  15

Ser Ser Asp Met Ser Cys Glu Arg Gly Arg His Gln Ser Leu Gln Cys
            20                  25                  30

Arg Ser Pro Glu Glu Gln Cys Leu Asp Val Val Thr His Trp Ile Gln
        35                  40                  45

Glu Gly Glu Glu Gly Arg Pro Lys Asp Asp Arg His Leu Arg Gly Cys
    50                  55                  60

Gly Tyr Leu Pro Gly Cys Pro Gly Ser Asn Gly Phe His Asn Asn Asp
65                  70                  75                  80

Thr Phe His Phe Leu Lys Cys Cys Asn Thr Thr Lys Cys Asn Glu Gly
                85                  90                  95

Pro Ile Leu Glu Leu Glu Asn Leu Pro Gln Asn Gly Arg Gln Cys Tyr
            100                 105                 110

Ser Cys Lys Gly Asn Ser Thr His Gly Cys Ser Ser Glu Glu Thr Phe
        115                 120                 125

Leu Ile Asp Cys Arg Gly Pro Met Asn Gln Cys Leu Val Ala Thr Gly
    130                 135                 140

Thr His Glu Pro Lys Asn Gln Ser Tyr Met Val Arg Gly Cys Ala Thr
145                 150                 155                 160

Ala Ser Met Cys Gln His Ala His Leu Gly Asp Ala Phe Ser Met Asn
                165                 170                 175

His Ile Asp Val Ser Cys Cys Thr Lys Ser Gly Cys Asn His Pro Asp
            180                 185                 190

Leu Asp Val Gln
        195
```

<210> SEQ ID NO 10
<211> LENGTH: 195
<212> TYPE: PRT
<213> ORGANISM: Homo sapiens

<400> SEQUENCE: 10

Val Thr Tyr Ser Arg Ser Arg Tyr Leu Glu Cys Ile Ser Cys Gly Ser
1               5                   10                  15

Ser Asp Met Ser Cys Glu Arg Gly Arg His Gln Ser Leu Gln Cys Arg
            20                  25                  30

Ser Pro Glu Glu Gln Cys Leu Asp Val Val Thr His Trp Ile Gln Glu
        35                  40                  45

Gly Glu Glu Gly Arg Pro Lys Asp Asp Arg His Leu Arg Gly Cys Gly
    50                  55                  60

Tyr Leu Pro Gly Cys Pro Gly Ser Asn Gly Phe His Asn Asn Asp Thr
65                  70                  75                  80

Phe His Phe Leu Lys Cys Cys Asn Thr Thr Lys Cys Asn Glu Gly Pro
                85                  90                  95

Ile Leu Glu Leu Glu Asn Leu Pro Gln Asn Gly Arg Gln Cys Tyr Ser
            100                 105                 110

Cys Lys Gly Asn Ser Thr His Gly Cys Ser Ser Glu Glu Thr Phe Leu
        115                 120                 125

Ile Asp Cys Arg Gly Pro Met Asn Gln Cys Leu Val Ala Thr Gly Thr
    130                 135                 140

His Glu Pro Lys Asn Gln Ser Tyr Met Val Arg Gly Cys Ala Thr Ala
145                 150                 155                 160

Ser Met Cys Gln His Ala His Leu Gly Asp Ala Phe Ser Met Asn His
                165                 170                 175

Ile Asp Val Ser Cys Cys Thr Lys Ser Gly Cys Asn His Pro Asp Leu
            180                 185                 190

Asp Val Gln
        195

<210> SEQ ID NO 11
<211> LENGTH: 194
<212> TYPE: PRT
<213> ORGANISM: Homo sapiens

<400> SEQUENCE: 11

Thr Tyr Ser Arg Ser Arg Tyr Leu Glu Cys Ile Ser Cys Gly Ser Ser
1               5                   10                  15

Asp Met Ser Cys Glu Arg Gly Arg His Gln Ser Leu Gln Cys Arg Ser
            20                  25                  30

Pro Glu Glu Gln Cys Leu Asp Val Val Thr His Trp Ile Gln Glu Gly
        35                  40                  45

Glu Glu Gly Arg Pro Lys Asp Asp Arg His Leu Arg Gly Cys Gly Tyr
    50                  55                  60

Leu Pro Gly Cys Pro Gly Ser Asn Gly Phe His Asn Asn Asp Thr Phe
65                  70                  75                  80

His Phe Leu Lys Cys Cys Asn Thr Thr Lys Cys Asn Glu Gly Pro Ile
                85                  90                  95

Leu Glu Leu Glu Asn Leu Pro Gln Asn Gly Arg Gln Cys Tyr Ser Cys
            100                 105                 110

Lys Gly Asn Ser Thr His Gly Cys Ser Ser Glu Glu Thr Phe Leu Ile
        115                 120                 125

Asp Cys Arg Gly Pro Met Asn Gln Cys Leu Val Ala Thr Gly Thr His
          130                 135                 140

Glu Pro Lys Asn Gln Ser Tyr Met Val Arg Gly Cys Ala Thr Ala Ser
145                 150                 155                 160

Met Cys Gln His Ala His Leu Gly Asp Ala Phe Ser Met Asn His Ile
                165                 170                 175

Asp Val Ser Cys Cys Thr Lys Ser Gly Cys Asn His Pro Asp Leu Asp
                180                 185                 190

Val Gln

<210> SEQ ID NO 12
<211> LENGTH: 193
<212> TYPE: PRT
<213> ORGANISM: Homo sapiens

<400> SEQUENCE: 12

Tyr Ser Arg Ser Arg Tyr Leu Glu Cys Ile Ser Cys Gly Ser Ser Asp
1               5                   10                  15

Met Ser Cys Glu Arg Gly Arg His Gln Ser Leu Gln Cys Arg Ser Pro
            20                  25                  30

Glu Glu Gln Cys Leu Asp Val Val Thr His Trp Ile Gln Glu Gly Glu
        35                  40                  45

Glu Gly Arg Pro Lys Asp Asp Arg His Leu Arg Gly Cys Gly Tyr Leu
    50                  55                  60

Pro Gly Cys Pro Gly Ser Asn Gly Phe His Asn Asn Asp Thr Phe His
65                  70                  75                  80

Phe Leu Lys Cys Cys Asn Thr Thr Lys Cys Asn Glu Gly Pro Ile Leu
                85                  90                  95

Glu Leu Glu Asn Leu Pro Gln Asn Gly Arg Gln Cys Tyr Ser Cys Lys
            100                 105                 110

Gly Asn Ser Thr His Gly Cys Ser Ser Glu Glu Thr Phe Leu Ile Asp
        115                 120                 125

Cys Arg Gly Pro Met Asn Gln Cys Leu Val Ala Thr Gly Thr His Glu
    130                 135                 140

Pro Lys Asn Gln Ser Tyr Met Val Arg Gly Cys Ala Thr Ala Ser Met
145                 150                 155                 160

Cys Gln His Ala His Leu Gly Asp Ala Phe Ser Met Asn His Ile Asp
                165                 170                 175

Val Ser Cys Cys Thr Lys Ser Gly Cys Asn His Pro Asp Leu Asp Val
            180                 185                 190

Gln

<210> SEQ ID NO 13
<211> LENGTH: 192
<212> TYPE: PRT
<213> ORGANISM: Homo sapiens

<400> SEQUENCE: 13

Ser Arg Ser Arg Tyr Leu Glu Cys Ile Ser Cys Gly Ser Ser Asp Met
1               5                   10                  15

Ser Cys Glu Arg Gly Arg His Gln Ser Leu Gln Cys Arg Ser Pro Glu
            20                  25                  30

Glu Gln Cys Leu Asp Val Val Thr His Trp Ile Gln Glu Gly Glu Glu
        35                  40                  45

Gly Arg Pro Lys Asp Asp Arg His Leu Arg Gly Cys Gly Tyr Leu Pro
    50                  55                  60

```
Gly Cys Pro Gly Ser Asn Gly Phe His Asn Asn Asp Thr Phe His Phe
65                  70                  75                  80

Leu Lys Cys Cys Asn Thr Thr Lys Cys Asn Glu Gly Pro Ile Leu Glu
                85                  90                  95

Leu Glu Asn Leu Pro Gln Asn Gly Arg Gln Cys Tyr Ser Cys Lys Gly
            100                 105                 110

Asn Ser Thr His Gly Cys Ser Ser Glu Glu Thr Phe Leu Ile Asp Cys
        115                 120                 125

Arg Gly Pro Met Asn Gln Cys Leu Val Ala Thr Gly Thr His Glu Pro
    130                 135                 140

Lys Asn Gln Ser Tyr Met Val Arg Gly Cys Ala Thr Ala Ser Met Cys
145                 150                 155                 160

Gln His Ala His Leu Gly Asp Ala Phe Ser Met Asn His Ile Asp Val
                165                 170                 175

Ser Cys Cys Thr Lys Ser Gly Cys Asn His Pro Asp Leu Asp Val Gln
            180                 185                 190

<210> SEQ ID NO 14
<211> LENGTH: 191
<212> TYPE: PRT
<213> ORGANISM: Homo sapiens

<400> SEQUENCE: 14

Arg Ser Arg Tyr Leu Glu Cys Ile Ser Cys Gly Ser Ser Asp Met Ser
1               5                   10                  15

Cys Glu Arg Gly Arg His Gln Ser Leu Gln Cys Arg Ser Pro Glu Glu
                20                  25                  30

Gln Cys Leu Asp Val Val Thr His Trp Ile Gln Glu Gly Glu Glu Gly
            35                  40                  45

Arg Pro Lys Asp Asp Arg His Leu Arg Gly Cys Gly Tyr Leu Pro Gly
    50                  55                  60

Cys Pro Gly Ser Asn Gly Phe His Asn Asn Asp Thr Phe His Phe Leu
65                  70                  75                  80

Lys Cys Cys Asn Thr Thr Lys Cys Asn Glu Gly Pro Ile Leu Glu Leu
                85                  90                  95

Glu Asn Leu Pro Gln Asn Gly Arg Gln Cys Tyr Ser Cys Lys Gly Asn
            100                 105                 110

Ser Thr His Gly Cys Ser Ser Glu Glu Thr Phe Leu Ile Asp Cys Arg
        115                 120                 125

Gly Pro Met Asn Gln Cys Leu Val Ala Thr Gly Thr His Glu Pro Lys
    130                 135                 140

Asn Gln Ser Tyr Met Val Arg Gly Cys Ala Thr Ala Ser Met Cys Gln
145                 150                 155                 160

His Ala His Leu Gly Asp Ala Phe Ser Met Asn His Ile Asp Val Ser
                165                 170                 175

Cys Cys Thr Lys Ser Gly Cys Asn His Pro Asp Leu Asp Val Gln
            180                 185                 190
```

ANTIBODY AGAINST UPA/UPAR

CROSS REFERENCE TO RELATED APPLICATION

This application is a 35 USC §371 National Phase Entry Application from PCT/EP02/00603, filed Jan. 22, 2002, and designating the U.S., which claims the benefit under 35 USC §119(e) of U.S. Provisional Application 60/263,198, filed Jan. 25, 2001.

The present invention provides methods and agents useful for the modulation of uPA/uPAR function, which can be employed in the diagnosis or therapy of several pathologies, including HIV infection, inflammation and cancer.

INTRODUCTION

Cell Migration and Disease

The human body responds to pathogenic stimuli by locally producing specific inflammatory molecules and recruiting specialized cells from blood and nearby tissues. This occurs in almost all diseases, and contributes in most cases to the general defenses of the organism. However, sometimes the inflammatory reaction, or the lack thereof, also contribute to the disease itself. Neutrophils, monocyte-macrophages, lymphocytes, endothelial cells, fibroblasts are attracted by specific migratory stimuli and build up a defense response that causes the destruction and elimination of the disease agent or organism. A series of severe pathological entities can be ascribed to excess or deficiency of the migratory cell response. For example, immunodeficiencies may be caused by a failure of the inflammatory cells to rush to the damaged or infected site. Cell recruitment in itself, on the other hand, may cause destructive pathologies in which autologous cells attack and destroy cells and tissues, as in some auto-immune diseases. It would be particularly advantageous to be able to know in advance such situations in order to take special precautions.

A special example among diseases is cancer. In this disease, a deficiency of the host lymphatic cells may be at the basis of the lack of humoral or cellular response against the cancer cells themselves, as it would be expected since cancer cells express very peculiar antigens. On the other hand, cancer cells have the particular ability to invade nearby tissues and to metastasize at a distance; this process, however, is due not only to a property of cancer cells. Indeed, non-malignant stromal host cells do actively participate in establishing the malignant and hence the destructive and invasive phenotype. While the mechanisms involved are still largely unknown, it is clear that a cooperation of stromal and cancer cells is required for the malignant phenotype, and that the stromal cells both respond to stimuli arriving from the cancer cells and signal to cancer cells. The pharmacological block of the invasive phenotype of cancer, must therefore rely on actions on both cancer and stromal cells. Again, it would be particularly advantageous to be able to know in advance the specific contributions of each type of cells.

Another special example is AIDS, a disease caused by HIV-1 and characterized by a progressive and severe immuno-deficiency and by a series of resultant deadly infections, tumors etc., caused by the immuno-deficiency itself.

Finally, infectious diseases have to be considered, since foreign bacteria recruit neutrophils and monocytes/macrophages to the site of infection.

Plasminogen Activator of the Urokinase-Type (uPA) and its Receptor (uPAR)

Urokinase-type plasminogen activator (uPA) is a serine protease that activates plasminogen to plasmin, a broad-spectrum serine protease itself. Plasmin is an important protease in fibrinolysis and its activity appears to be required also in wound healing.

UPA is synthesized as an inactive precursor (pro-uPA) that undergoes proteolytic activation to uPA. Pro-uPA (and uPA) bind with high affinity (Kd of 0.1 nM) (Stoppelli, 1985; Vassalli, 1985) to a specific plasma membrane receptor (uPAR, CD87) that localizes its activity to the cell surface, thus restricting the area of activation of plasminogen (Stephens et al., 1989). The molecule of uPA can be divided in two fragments, each endowed with a specific activity: the amino terminal fragment (ATF) has the receptor-binding activity, the carboxy-terminal fragment (also called low molecular weight urokinase) has the full proteolytic activity.

UPAR (Dano, 1990) is a molecule present on the cell surface and formed by three repeats, characterized by a specific-disulfides-pattern (see FIG. 1 for a scheme). The three repeats, of about 90 residues each, are connected by two linker regions and define specific protein domains. The amino-terminal domain, D1, has been shown to bind uPA directly, although other areas of the receptor (like domain D3) are also relevant in contacting uPA. uPAR is bound to the cell surface with a specific glycosyl-phosphatidylinositol (GPI) anchor, and hence lacks a trans-membrane and an intracellular moiety which would be typical of other receptors. Importantly (see below), the linker region between domain D1 and D2 contains a sequence, AVTYSRSRYLEC [SEQ ID NO: 11], to which a chemotactic epitope has been mapped (Blasi, 1997; Fazioli, 1997; Nguyen, 2000).

Ligands of uPAR

In addition to specifically binding uPA, uPAR is able to also bind vitronectin, hence being able to provide an anchorage to the cells when plated on vitronectin (Deng et al., 1996; Hoyer-Hansen, 1997; Sidenius, 2000; Waltz, 1994). In addition, uPAR has been reported to interact with other molecules, like thrombospondin (Higazi et al., 1996), kininogen (Colman et al., 1997), although at lower affinity. Important among these appear to be the interactions with integrins (Simon, 2000; Tarui, 2000; Waltz et al., 1997; Wei et al., 1996; Xue et al., 1994; Xue et al., 1997; Yebra et al., 1996). The interaction with integrins appears to have signaling properties, since it can affect cell adhesion (Wei et al., 1996) and cell migration (Degryse, 1999; Degryse, 2001; Yebra et al., 1996). Finally, interactions with other cell surface proteins like the mannose-6-phosphate receptor (Nykjaer, 1998) and the uPARAP (Behrendt, 2000) have been reported.

UPAR and Signaling

In the last few years it has been convincingly shown that uPAR is a signaling receptor when it is activated by uPA. In this respect, the catalytic activity of uPA in some cases does not appear to be required. Binding of uPA to uPAR induces cell migration, cell adhesion and proliferation (Blasi, 1997; Chapman, 1997; Ossowski, 2000). A. Cell migration appears to be induced at physiological expression levels of uPAR, while cell adhesion and proliferation appear to require high levels of receptors, as those present in cancer or in transfected cells (Ossowski, 2000). In line with this possibility, mice lacking uPA or uPAR have a strong immunodeficient phenotype due to lack of migration of several inflammatory cells, and are unable to fight infection by C. neoformans and P. aeruginosa (Gyetko, 1996; Gyetko, 2000). The migration-promoting activity of uPAR requires binding of uPA and is mediated by a pertussis toxin-sensitive receptor and requires the activation of a Src-family tyrosine kinase, and of ERKs (Fazioli, 1997; Nguyen, 2000; Ossowski, 2000; Resnati, 1996). Importantly, infection with B. The cell adhesion properties of uPAR are mediated by a lateral interaction with at least some of the cytoskeleton-engaged integrins and are mediated by caveolin (Wei et al., 1996; Wei et al., 1999). C. The proliferation properties, on the other hand, depend on a constitutive engagement of an α4-integrin by uPAR, resulting in constitutive activation of the proliferation-promoting ERK and inhibition of the growth-inhibiting p38-MAP kinase (Aguirre Ghiso et al., 1999; Ossowski, 2000).

UPAR and Cell Migration

Exogenous uPA induces chemotaxis in a variety of cells (Boyle, 1987; Degryse, 1999; Fibbi, 1988; Gudewicz, 1987; Gyetko, 1994; Nguyen, 2000; Resnati, 1996; Webb et al., 2000). In-depth studies have shown that uPA binding transforms uPAR into a ligand for a cell surface protein which can transducer its signal (Blasi, 1997). Upon binding of u-PA, a peptide epitope of u-PAR, which is otherwise hidden in the context of the molecule, comes at the surface of the molecule or becomes available because of cleavage of uPAR. The peptide has the sequence AVTYSRSRYLEC [SEQ ID NO: 1] (FIG. 1), and is located in the region linking domain D1 to D2 and endowed with chemotactic activity (Blasi, 1997; Fazioli, 1997). Recombinant fragments of u-PAR containing at least the SRSRY [SEQ ID NO: 2] sequence ("activated" uPAR) induce migration in uPAR-lacking cells (Blasi, 1997; Fazioli, 1997). The chemotactic epitope of u-PAR remains active whether placed at the N- or at the C-terminal end of a recombinant fragment. Indeed, both domain D1-SRSRY [SEQ ID NO: 2] or SRSRY-domain D2-D3 [SEQ ID NO: 2] are both chemotactically active (Blasi, 1997; Fazioli, 1997). Synthetic peptides containing at least the SRSRY [SEQ ID NO: 2] sequence can efficiently substitute for uPA-uPAR interactions or for the addition of exogenous activated uPAR fragments (B. Degryse, 1999; Blasi, 1997; Fazioli, 1997).

The uPAR-Adapter

Since uPAR lacks an intracellular domain, a trans-membrane adapter has been suggested to mediate the signaling effects of uPA/uPAR (Resnati, 1996). The best evidence for the existence of an adapter is the finding that in cells lacking uPAR, a soluble modified form of uPAR can directly act as a chemoattractant. A sequence between domain D1 and D2 of uPAR has been shown to be responsible for this activity. In fact, a synthetic peptide corresponding to this region or the uPAR fragment carrying this peptide at the amino terminus (henceforth called "D2D3$_{88-278}$") has a very potent chemotactic activity and reproduces the signaling events evoked by uPA (Blasi, 1997; Fazioli, 1997; Nguyen, 2000). Chemotaxis induced by uPA and D2D3$_{88-279}$ in peripheral blood monocytes, in THP-1 myeloid precursors leukemic cells, cancer cells and smooth muscle cells is pertussis-toxin sensitive and induces Hck and MEK phosphorylatlon. The later are required for activity (Degryse, 2001; Nguyen, 2000; Resnati, 1996; Webb et al., 2000).

UPA/uPAR and Cancer

It is a long time that pro-uPA, uPA and uPAR are known to be involved in the pathogenesis and malignancy of cancer and this knowledge is based upon: 1. uPA and uPAR are almost constantly overexpressed in human and model cancers (rev. in Ossowski, 2000). 2. Several approaches have shown that inhibition of uPA activity or of uPAR binding reduces the invasiveness of tumor cells in murine models of cancer in vivo, while overexpression increases it considerably (Crowley, 1993; Min, 1996; Ossowski, 1991; Ossowski, 1988; Ossowski, 2000). 3. High levels of pro-uPA or uPAR in tissues, serum or urine are a major negative prognostic marker in human cancer (Sier, 1998; Sier, 1999; Stephens, 1999).

UPA/uPAR and Inflammatory Diseases

Upon cell stimulation, u-PAR is expressed by circulating monocytes, neutrophils and T-lymphocytes but not by erythrocytes nor B-lymphocytes (Bianchi et al., 1996; Todd, 1985). In addition, u-PAR (CD87) is a target gene in lymphocytes and macrophage activation (Cao et al., 1995; Nykjaer, 1994). Indeed, monocytes and monocyte-like cells (like HL60, U937) express u-PAR, or are induced to overexpress u-PAR by a variety of cytokines and other agents, like phorbol ester PMA, phytohemagglutinin, bacterial liposaccharide, TGFβ1/vitamin D3, GM-CSF, IFN, TNFα etc. In human T-lymphocytes, stimulation of the TCR/CD3 complex, treatment with lymphokines IL2, IL4, IL7 or the concomitant activation of the T cell receptor and integrins engagement, all induce u-PAR expression (Bianchi et al., 1996; Nykjaer, 1994). It is also noteworthy, that u-PAR is expressed by tumor infiltrating T-lymphocytes and the migration of activated T-lymphocytes through reconstituted basement membranes, is at least in part, u-PA- and u-PAR-dependent (Bianchi et al., 1996). In view of the important contribution of stromal cells to the invasiveness of cancer, it is also important to stress that in human tumors one of the cells that more than the others contributes to the overall u-PAR production is the tumor macrophage (Dano, 1994). Very importantly, uPAR expression is up-regulated by the infection of cells with the Spirochete Borrelia burgdorferi, the etiologic agent of Lyme disease, a pathogen that acquires uPA on its surface hence acquiring invasive properties. Likewise, exposure of cells to Salmonella typhimurium and Streptococcus pyogenes results in up-regulation of uPAR (Coleman JL, 2001). Lyme disease is characterized by inflammatory manifestations in skin, heart, CNS and joints, resulting inn tissue damage due to infiltration of inflammatory cells, primarily monocytes/macrophages. Interestingly, lipidated OspA hexapeptide from B. burgdorferi, as well as liposaccharide from S. typhimurium and lipotechoic acid from S. pyogenes were able to induce the release of suPAR from human U937 cells (Coleman JL, 2001).

It is a long time that uPA and uPAR are known to be involved in inflammation. First, both molecules are upregulated by inflammatory agents, like the endotoxin liposaccharide or IL1-β (Hasegawa, 1997). Moreover, uPA and uPAR activate typical inflammatory reactions like migration (Sitrin, 2000; Sitrin et al., 1999) and superoxide anion release (Cao et al., 1995) in neutrophils. Increase of uPA and uPAR has been shown in diseases with major inflammatory components like Crohn's disease (Desreumaux, 1999), inflammatory joint diseases (Cerinic, 1998; Del Rosso, 1999), rheumatoid arthritis (Braat and D.C., 2000; Slot, 2000; Slot, 1999) and Lyme disease (Coleman JL, 2001). Moreover, in murine models uPA and uPAR have been shown to be essential components in the response to pneumocistis carinii (Beck, 1999), in arthritis models (Busso N, 1998), in several vascular aspects of inflammation (Carmeliet P, 1997) and in peritoneal inflammation (May et al., 1998). Finally, uPA/uPA. are expressed in differentiating dendritic cells and down regulated in the final stages of differentiation (Ferrero, 2000).

Also in cancer cells, despite u-PAR is often expressed in stromal cells, u-PA and u-PAR can influence the migration of cancer cells. The "activation" of u-PAR on stromal cells can attract cancer cells through a chemokine-like action. In this case u-PAR would behave as a cell-surface chemokine.

Indeed, chemokines anchored to a presentation molecule present in the extracellular matrix can attract other cells having specific receptors (Premack, 1996). Since uPAR is itself a membrane protein, it may not require a presentation molecule.

Release of Soluble u-PAR in the Circulation in Human Diseases

Many receptors are found in blood. U-PAR makes no exception. It has been first found in the blood and ascitic fluid of ovarian cancer patients (Pedersen, 1993) and subsequently in tissues, blood or even urine of many other types of cancer, including leukemias. In most cases high levels of released su-PAR can be related to poor prognosis (Stephens, 1999). Also in other diseases, su-PAR level is increased in tissues or blood: i.e. Rheumatoid Arthritis (Slot, 2000; Slot, 1999) and particularly in AIDS (see below). Release of soluble uPAR was also observed upon infection of cells to Borrelia burgdorferi, Salmonella typhimurium and Streptococcus pyogenes (Coleman JL, 2001).

UPA/uPAR and AIDS

Multiple evidence ties together uPA and uPAR with the HIV and AIDS. First, uPA and uPAR ecpression on T lymphocytes and monocytes is modulated by HIV infection (Speth, 1998) and uPAR is an activation antigen in T cells and is increased in AIDS patients (Nykjaer, 1994). Finally, it has been shown that uPA can directly cleave the viral gp120 in the V loop, important for viral infection (Handley, 1996).

We have recently measured the level of soluble uPAR (suPAR) in the blood of a well defined, large cohort of HIV-positive individuals drawn prior to the introduction of the highly active anti-retroviral therapy regimens. In this cohort, the level of suPAR was found to be proportional to the severity of the disease state (i.e. serum-positive v. immuno-deficient v. AIDS) and was an extremely significant negative prognostic indicator (Sidenius, 2000). The prognostic significance of the levels of suPAR was independent of, and as indicative as, the decrease of $CD4^+$ T-lymphocytes or a very high viremia. A low level of suPAR was found to be a good prognostic marker even in patients with high viremia and low $CD4^+$ cells. Conversely, a high level of suPAR was a negative indicator even in patients with relatively high $CD4^+$ cells and low viremia. The statistical significance of these correlations (Sidenius, 2000) suggests that the uPA/uPAR system may somehow intervene in the pathogenesis of AIDS.

U-PAR Fragments and Human Diseases

In addition to an intact su-PAR (Sier, 1998), fragments of su-PAR are often found in cancer tissue and in cell lines. From their size and from their antibody reactivity these fragments correspond roughly to either a released domain D1 or to a released or cell-bound domain D2-plus-D3 (Hoyer-Hansen, 1997; Hoyer-Hansen, 1992; Mustjoki, 2000; Solberg, 1994). Moreover, these fragments are also found in the conditioned media of, for example, U937 cells and their abundance relative to the intact su-PAR appears to be controlled (Sidenius, 2000).

The discovery that those fragments of u-PAR that contain at their N- or C-termini the SRSRY [SEQ ID NO: 2] minimal epitope have potent chemotactic activity (Blasi, 1997; Faziolo, 1997), demonstrates that some of the fragments which are produced in vivo may in fact be "activated" u-PAR molecules. Their production in a given tissue can profoundly change the migratory potential of the cells present in that issue. Hence, it is very important to identify if such in vivo u-PAR fragments represent in fact "activated" u-PAR. Such fragments have been found in serum or in tissues at low levels in the urine of normal individual (Sidenius, 2000) and at high levels in diseases such as leukemia (blood) (Mustjoki, 2000) and cancer (urine and tissues but not blood) (Sidenius, 2001), and may possibly be found in many others. In healthy individuals such fragments have never been found in the blood, and are present in very low amounts in their tissues and urine. However, the presence of the chemotactic epitope in these fragments cannot be evaluated except by complex methods involving protein purification and sequencing.

U-PAR is very resistant to proteases with the exception of the linker region between domain D1 and D2 (Behrendt, 1991). This region can be cleaved in vitro by several proteases. Cleavage in this region results in the production of two unequal fragments of u-PAR, one containing domain D1, the other domain D2-plus-D3. The nature of the cleaving protease will determine whether and how much of the chemotactic epitope is preserved in the u-PAR fragments (FIG. 1). For example, chymotrypsin cleaves between residue 87 and 88, leaving a D2-plus-D3 fragment with the SRSRYLEC [SEQ ID NO: 3] amino terminus. This "activated" uPAR, when prepared in soluble form, has a very potent chemotactic activity on several cells and cell lines (Blasi, 1997; Fazioli, 1997). Also uPA itself cleaves uPAR, at residue 84, producing a D2-plus-D3 fragment with an amino terminal AVTYSRSRYLEC [SEQ ID NO: 4] sequence (Hoyer-Hansen, 1997; Hoyer-Hansen, 1992). Again, this fragment is endowed with a very strong chemotactic activity. The synthetic peptide AVTYSRSRYLEC [SEQ ID NO: 4] also has an extremely potent chemoattractant activity, such as shorter peptides that still contain the SRSRY [SEQ ID NO: 2] sequence (Blasi, 1997; Fazioli, 1997). Alternatively, enzymes like plasmin can probably destroy the epitope as they cleave at both residue 90 and 92, i.e. within the SRSRY [SEQ ID NO: 2] region (Resnati et al., 1996).

The fact that u-PAR fragments are produced in vivo, and that their level is increased in several diseases suggests that they can be part of the disease itself. Hence, it will be important to measure their level and their molecular nature.

DESCRIPTION OF THE INVENTION

1. Pro-uPA and its Analogs/derivatives Inhibit HIV-infection and the Reactivation of Latent HIV The present invention relates to the effect of pro-uPA on the reactivation of latent HIV-1 or on the infection and replication of HIV-1 in human cells. U1 cells harbour a latent HIV-1 which can be reactivated by various cytokines. In these cells, the proenzyme form (pro-uPA) of urokinase plasminogen activator (uPA) prevents the reactivation of HIV replication induced by PMA or TNF-alpha, and synergizes with anti-TNF-alpha antibodies and with TGF-beta in totally blocking this reactivation. In addition, pro-uPA also blocks the entry/infection of HIV in peripheral blood mononuclear cells (PBMC) without affecting cell proliferation. In accordance with these results, we have found that the U937 cells clones which sustain a rapid and efficient proliferation of HIV upon infection ("plus" clones) display high levels of uPAR. On the contrary, other clones which show a much delayed and inefficient production of virus ("minus" clones) display a very low level of uPAR. Pro-uPA can be used together with other drugs to block HIV infection or its spreading.

2. The Seven Trans-membrane Receptor FPRL1/LXA4R Mediates the Chemotactic Activity of uPAR Since uPAR has no trans-membrane domain, it cannot directly transmit to the cell the signal given by the binding of uPA. The pertussis toxin sensitivity indicates that a G protein-coupled, seven trans-membrane receptor, is involved. To identify this adapter, we have searched for a cell line in which to introduce candidate adapters' cDNAs and test their responase to D2D3$_{88-278}$ in chemotaxis. An helpful information was available in the literature, which has focused our attention to the receptors for the bacterial chemotactic peptide fMLP. Indeed, chemotaxis by fMLP has been reported to require uPAR (Gyetko, 1994). Chemotaxis by fMLP is induced by two seven transmembrane receptors, one of high affinity, FPR, and one of low affinity, FPRL1 (Prosnitz, 1997) (Murphy, 1996). The low affinity FPRL1 receptor also binds specifically to other ligands like lipoxin A4 (and hence it is also called LXAR) (Gronert, 1998), serum amyloid A (Su, 1999), LL-37 cathelicidin (Yang et al., 1999), and several peptides including some derived from HIV gp120 and gp41 (Chiang, 2000; Deng, 1999; Le, 1999). Interestingly, it appears that multiple signaling pathways can be activated through FPRL1/LXA4R, depending on the ligand (Chiang, 2000).

Here we identify a seven trans-membrane, G-protein-coupled receptor, FPRL1/LXA4R, as the mediator of uPAR chemotactic activity. The inhibition of FPRL1/LXA4R reduces the inflammatory effects of uPA/uPAR. Hence, FPRL1/LXA4R constitues a novel target for anti inflammatory therapy. Since uPA/uPAR are also involved in the migration of cancer cells, and hence of their invasiveness and metastasis, FPRL1/LXA4R becomes a novel target for anti-metastatic therapy. In all these cases, the inhibitors would act at a step subsequent to the binding of uPA to uPAR.

3. Antibodies to the Seven Trans-membrane, G-protein Coupled FPRL1/LXA4R Receptor Inhibit the uPA/uPAR Chemotactic and Migration-promoting Activity The present invention also regards the identification of a first inhibitor of the membrane mediator of the migration-promoting activity of uPA/uPAR, i.e. of FPRL1/LXA4R. FPRL1/LXA4R can bind multiple ligands. These include the formul peptides (at high concentrations), lipoxin A4 and its analogs, various peptides of the HIV proteins gp120 and gp41l, and proteins that works however in general at high concentrations. In addition, this receptor binds also a specific antibody raised against peptide ASWGGTPEERLK [SEQ ID NO: 4] in the third extracellular domain of FPRL1/LXA4R (Fiore, 1995).

Antibodies to the FPRL1/LXA4R receptor specifically block migration of human freshly isolated monocytes or of leukemic THP-1 cells induced by ATF/uPA-pro-uPA and mediated by uPAR binding. They also inhibit the chemotactic activity of the "activated" uPAR fragment D2D3$_{88-278}$. Such antibodies, in suitable pharmaceutical compositions, can be specifically used to arrest cell migration in hyper-inflammatory diseases like Crohn's disease, septic shock, rheumatoid arthritis, cancer and AIDS.

4. Antibodies and ELISA to Specifically Recognize Cleaved, "Activated" Forms of uPAR and to Inhibit uPA/uPAR Induced Migration Polyclonal antibodies raised against the chemotactically active sequence AVTYSRSRYLEC [SEQ ID NO: 1] specifically recognize cleaved ("activated") forms of u-PAR containing residues 84 and/or 85, and/or 86, and/or 87 at the amino terminus. Antibodies generated by injecting the peptide AVTYSRSRYLEC [SEQ ID NO: 1] into rabbits were found to be unable to recognize intact, full-length su-PAR. However, they identified cleaved form of D2-plus-D3 that contain at their N-termini the AVTYSRSRYLEC [SEQ ID NO: 1], or VTYSRSRYLEC [SEQ ID NO: 5] or TYSRSRYLEC [SEQ ID NO: 6] or YSRSRYLEC [SEQ ID NO: 7] at the amino terminus. The antiserum did not recognize fragments with amino-terminal SRSRYLEC [SEQ ID NO: 3] obtained by cleavage with chymotrypsin. An ELISA assay capable of specifically quantitating the concentration of D2-plus-D3 is reported. Therefore, other antibodies (such as monoclonal antibodies) can be generated to specifically identify all possible fragments of D2 plus D3 relevant for human diseases.

The present invention provides a method to identify and quantitate the presence of activated forms of u-PAR, the receptor for u-PA, the urokinase-type plasminogen activator. Thie method comprises the production of antibodies that specifically identify the presence in tissues, in extracts, in biological fluids of natural or recombinant forms of u-PAR which contain at their termini the chemotactic peptide of u-PAR. The method also comprises the set-up of an ELISA (Enzyme-Linked Immuno-Sorbent Assay) to quantitatively assess in absolute or percentile terms the presence of said forms of u-PAR. The use of these method and reagents is important in a variety of diseases caused by deficient or excessive cell migration, where the production of activated forms of u-PAR is required.

DESCRIPTION OF THE FIGURES

FIG. 3. —The anti-HIV effect of proUPA is reverted by R3, R4 and R5 antibodies in U1 cells. Data are shown as average and STD of duplicates collected at peak of HIV expression (day 4), measured as RT activity (cpm/µl). a-TNP is an isotype-matched control.

FIG. 8A. —The ability of HIV-1 to replicate in different clones of U937 cell correlates with the level of expression of uPAR, as measured by ELISA. The "plus" clones (+) are those that replicate very efficiently and rapidly (2-3 weeks). The "minus" (−) clones replicate very inefficiently and slowly (6 to 7 weeks). PMA, when used, was at 10 nM.

FIG. 14. —Anti-FPRL1/LXA4R antibodies specifically inhibit ATF-induced chemotaxis. Antibody was diluted 1:20, but works as well also at 1:100.

EXAMPLE 1

Figure 1:
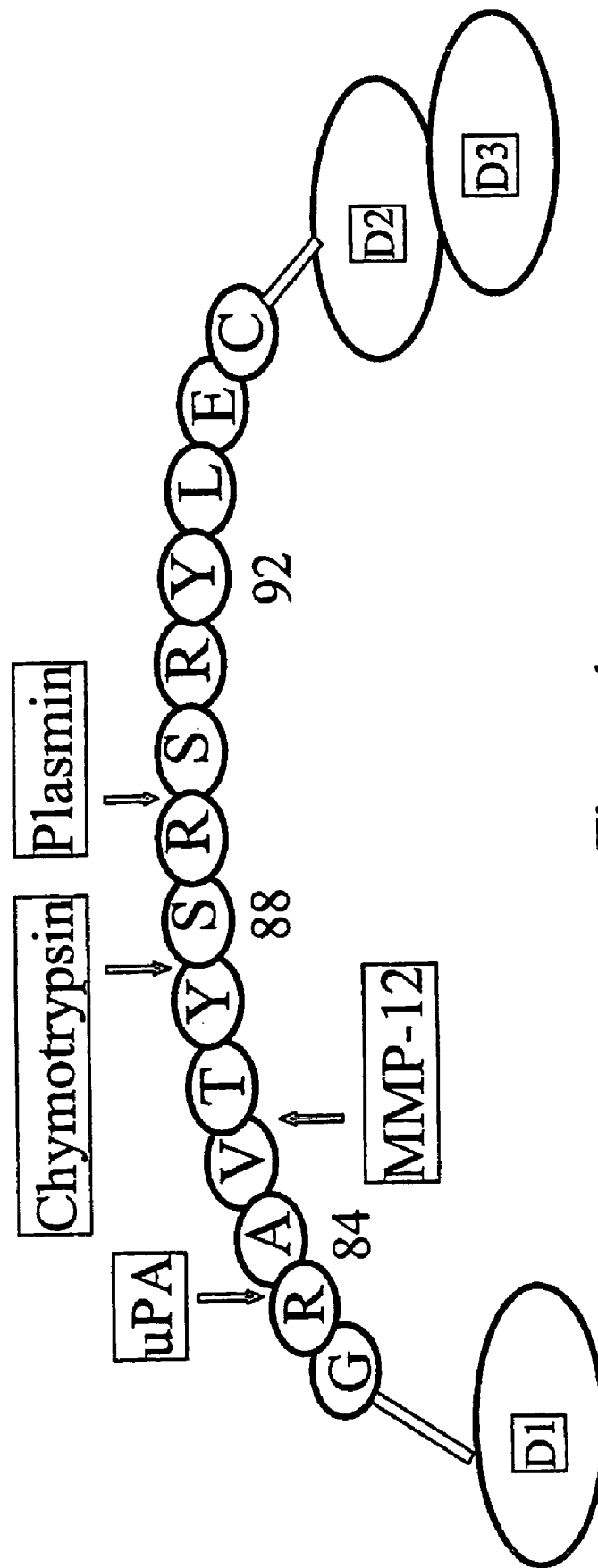
FIG. 1. —A scheme of the structure if uPAR. This is composed of three domains, D1, D2 and D3. The linker region between domain D1 and D2 [SEQ ID NO: 8] starts at Gly 83. UPA can cleave between residues Arg84 and Ala85, MMP-12 between Thr86 and Tyr87, chymotrypsin between Tyr87 and Ser88 and plasmin between Arg89 and Ser90. Domain D3 is connected to the cell surface by a GPI anchor.

Pro-urokinase (pro-uPA) and its derivatives uPA and ATF, inhibit the replication of HIV-1 in latently infected monocytoid cell lines and in freshly infected human blood cells.

Latent HIV infected cells provide a cellular population resistant to anti-retroviral therapy and represent the mechanism for lifelong persistence of HIV (Finzi et al., 1999). The promonocytic U937 cell line is one of the most utilized models for studies on in vitro HIV infection. It displays both CD4 and CXCR4 and, therefore, can be infected by X4 viruses. From this cell line has been derived the chronically infected cell line named "U1", containing two copies of integrated proviruses, and broadly used as a model of viral latency and reactivation (Folks et al., 1988). The U1 promonocytic cell line is one of the most thoroughly characterized models of post-integration latency. It was obtained from a population of U937 cells surviving the cytopathic effect of acute infection by HIV-1$_{LAI/IIIB}$ (X4), and contains two copies of integrated proviruses (Folks et al., 1987; Folks et al., 1988). In the absence of stimulation, U1 cells expresses low levels of multiply spliced 2 kb HIV-1 transcript (Butera et al., 1994) encoding the regulatory proteins Tat, Rev and Nef (Pomerantz et al., 1990). Several studies have subsequently demonstrated that the state of relative latency in U1 cells is a consequence of defective Tat function (Cannon et al., 1994; Emiliani et al., 1996). High levels of virus production can be rapidly induced by stimulation of U1 cells with proinflammatory cytokines, such as tumor necrosis factor-α (TNF-α), IL-6, IL-1β (Vicenzi et al., 1997), through the activation of MAPK and consequent stimulation of AP-1 and NF-κB (Yang et al., 1999). Alternatively, reactivation of virus replication can also be achieved by production of endothelium-derived soluble factors including MCP-1, TNF-α and IL-6 (Borghi et al., 2000), and by chemical agents such as phorbol-myristate acetate (PMA) (Folks et al., 1988). In addition to HIV-inducing agents, inhibitor agents have also been reported. These include the interferon-inducible double-stranded RNA dependent p68 protein kinase that inhibits TNF-α-induced HIV replication (Muto et al., 1999), and TGF-β that inhibits PMA-induced HIV expression (Poli et al., 1991).

It has been previously reported that different clones of U937 cells, originated by limiting dilution, could be divided in two distinct categories named "Plus" and "Minus", to describe their differential ability of sustaining productive HIV infection. Infection of plus clones typically shows a peak of virus replication between the second and the third weak, whereas minus clones are substantially delayed (typically, the peak of virus replication is observed after 6-9 weeks from infection) and sometimes with very low levels of virus production (Franzoso et al., 1994). We have measured the levels of uPAR in "plus" and "minus" clones and correlated thse values with the ability to sustain viral replication. We find that low levels of uPAR correlate with high levels of viral replication.

Materials and Methods

Reagents uPA, uPAR, suPAR, LMW-uPA, ATF, R2, R3, R4, R5 antibodies have been thoroughly described in the literature (Blasi, 1994; Rønne, 1991). Phorbol-myristate acetate (PMA) (Sigma, Milano, Italy) was used at $10^{-8}$ M, recombinant IL-6, TGF-β, TNF-α and polyclonal antibody antiTNF-α and isotype were purchased from R&D Systems (Minneapolis, Minn.) and used at the final concentrations of 10, 5 and 1 ng/ml, and 1 µg/ml respectively, as previously reported (Poli, 1990; Poli et al., 1990).

Cell Proliferation

Cell proliferation was assessed using $^3$H-thymidine uptake assay. One µCi of $^3$H-thymidine was added to $2 \times 10^4$ cells in 100 µl medium and incubated 16 h at 37° C., 5% $CO_2$. Cells were harvested and counted in a β-counter (TopCount, Packard, Downers Grove, Ill.).

Cell Lines p U1 cells were stimulated at the density of $2 \times 10^5$ cells per ml in RPMI 1640 (Whittaker M. A. Bioproducts, Walkerville, Md.) containing 10% FCS. Cells were pre-incubated with uPA, uPAR, suPA, R2, R3, R4, R5 antibodies for 20 min at 37° C. prior to addition of stimuli. U1 parental cell line U937 was used as a control in the transfection experiments. U937 cells were purchased from ATCC and maintained in RPMI 1640 medium in the presence of FCS before and after infection with the X4 HIV-1$_{LAI/IIIB}$. For infection, cells were seeded at $2 \times 10^5$ cells/ml in 96-well flat bottomed plates (Falcon, Becton-Dickinson Labware, Lincoln Park, N.J.) and infected with $1-2 \times 10^7$ virus particles diluted from a stock of pelleted virus (Advanced Biotechnology, Inc., Columbia, Md.). After infection, 2 h at 37° C., cells were washed and resuspended in RPMI 1640 medium.

Viral expression was monitored by determination of $Mg^{2+}$-dependent Reverse Trascriptase (RT) activity in culture supernatants (Poli, 1990). In particular, 5 microliters of supernatants was added to 25 microliters of a mixture containing poly(A), oligo(dT) (Pharmacia Fine Chemicals, Piscataway, N.J.), MgC12, and 32P-labeled deoxythymidine 5'-triphosphate (dTTP) (Amersham Corp., Arlington Heights, Ill.), and incubated for 2 h at 37°°C. 6 microliters of the mixture was spotted onto DE81 paper, air dried, washed five times in 2× SSC buffer, and two additional times in 95% ethanol. The paper was then dried and counted on a scintillation counter (LS 5000, Beckman Instruments, Inc., Fullerton, Calif.).

Viruses

Two R5 HIV-1 strains were used in this study, ADA and Bal. Both HIV-1 stocks were prepared in primary PBMC, supernatants were filtered, 0.2 µm, aliquoted and stored at −80° C.

Preparation of Primary Cells and Infection Conditions

PBMC were obtained from Ficoll-Hypaque (Amersham Pharmacia, Uppsala, Sweden) separated blood of seronegative donors, resupended in RPMI 1640 containing 10% FCS and allowed to activate by PHA (5 micrograms per ml) (Sigma, Milian, Italy) or IL-2 (20 Units per ml) (Chiron, Emeryville, Calif.). After 3 days cells were washed and resuspended in medium containing IL-2.

MDM cells: PBMC were separated onto an isoosmotic Percoll gradient (Amersham Pharmacia). Purity was consitently >90%, as determined by FACS analysis of CD14 expression. Monocytes were seeded in 48-well plastic plates (Falcon, Becton Dickinson Labware) at one milion per ml in DMEM (BioWhittaker) supplemented with 10% FCS (Hyclone) and 5% pooled human serum, and allowed to differentiate for 5-7 days. Media and sera were monitored for low content of endotoxin by the Limulus amoebocyte lysate assay (BioWhittaker).

Before infection cells were pretreated with proUPA (at 37° C. and 5% CO2) for 10 minutes, at the indicated concentration. Primary cells were infected with 0,1 MOI of an R5 HIV strain. After two hours of adsorption, at 37° C. and 5% CO2, virus was extensively washed out and medium containing new aliquot of proUPA was added. Fifty percent of culture medium was changed every 3 days and new medium containing proUPA was added back.

Measurement of uPAR Antigen

Cells were harvested by centrifugation, washed twice with PBS, and lysed in PBS containing 1% Triton X-100. The total protein concentration was determined using a kit (Dc Protein Assay, BIO-RAD) with BSA as standard, and concentration of uPAR antigen by a commercial uPAR ELISA kit (UR-1, Monozyme, Denmark).

Statistical Analysis

For all experiments, culture supernatants were collected every day for five days, in the case of cell line, or every three days for infection of U937 and primary cells. Reagents were replenished every time culture medium was changed. Data representative of one out of three independent experiments are shown. Results are presented as means of triplicate cultures, and the error bar show the standard deviation from the mean.

Results a. Pro-uPA and ATF inhibit HIV-1 expression in PMA and TNFalpha, but not IL-6, stimulated U1 cells.

Figure 2:
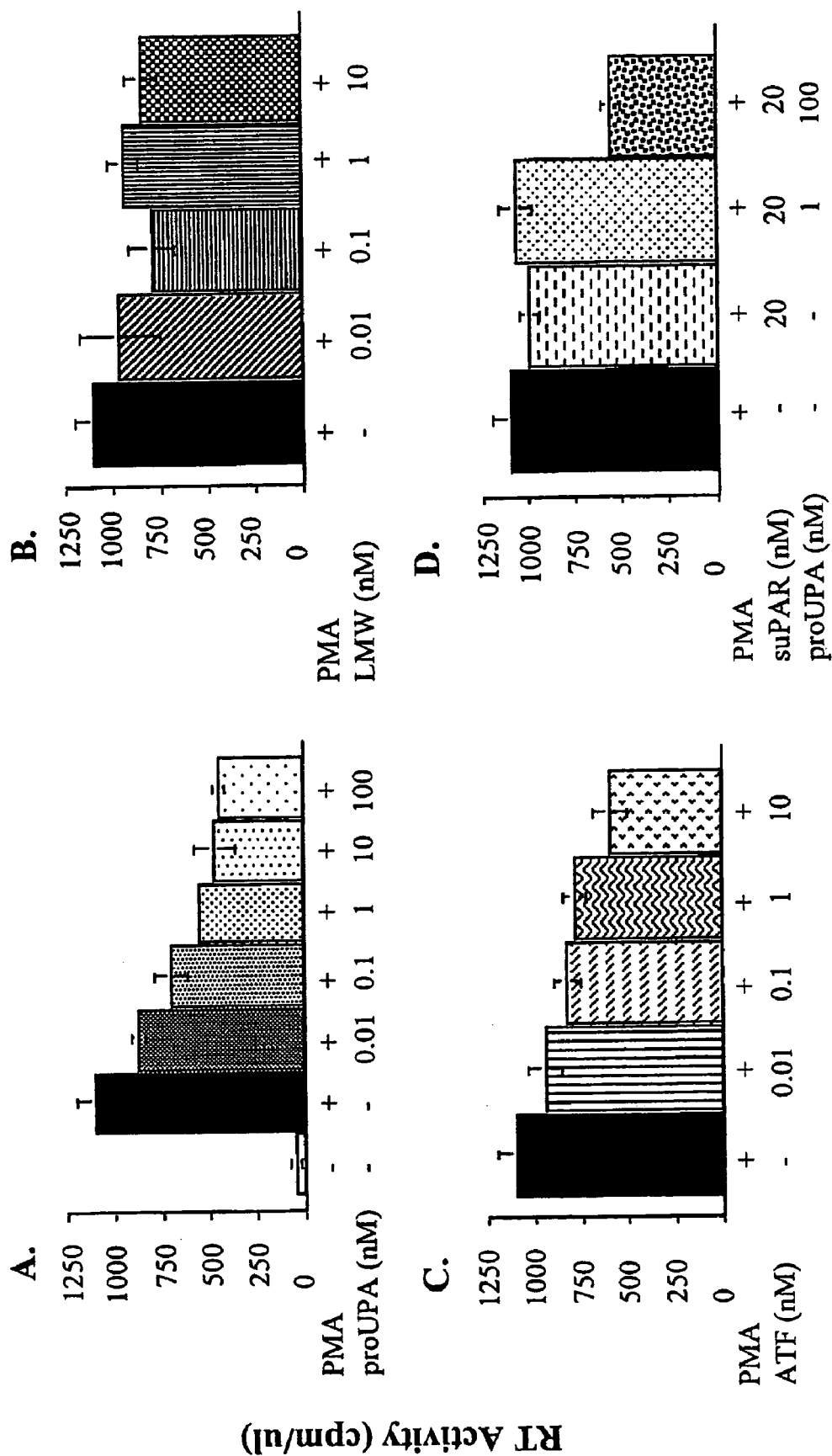
FIG. 2. —Pro-uPA and ATF, but not LMW uPA, inhibit HIV-1 reactivation induced by PMA (10 nM) in U1 cells. SuPAR blocks the effect of pro-uPA.Pro-uPA and other effectors added at zero time.

We have tested whether pro-uPA interferes with the induction of HIV-1 by various cytokines. As shown in FIG. 2A, treatment with pro-uPA causes a concentration-dependent decrease of PMA-induced HIV-1 replication as measured by RT activity. Inhibition is not complete, reaching about 60% at 1-10 nM pro-uPA. The effect of pro-uPA is specific as can be blocked by a recombinant suPAR (soluble uPAR) which specifically binds pro-uPA preventing its association to the cell surface uPAR (FIG. 2D). The effect of pro-uPA might be due to its conversion to uPA and subsequent plasmin formation from serum plasminogen. Alternatively, it might act by binding to uPAR inducing a signal-transduction pathway in competition with PMA. The inhibition of pro-uPA effect by suPAR suggests the latter possibility, suPAR acting as a pro-uPA scavenger, since the pro-uPA-suPAR complex is still enzymatically active but unable to bind cell surface uPAR. To confirm this possibility, we tested both LMW uPA and ATF. LMW-uPA is the carboxyl-terminal domain of uPA with full enzymatic activity and no receptor binding affinity. ATF is the amino terminal fragment of uPA with full receptor-binding and no enzymatic activity (Stoppelli, 1985). As shown in FIG. 2B, LMW uPA does not inhibit PMA-induced HIV-1 expression. On the other hand, ATF fully reproduces the pro-uPA effect (FIG. 2C). Overall, these data suggest that pro-uPA inhibition of PMA-induced HIV-1 expression requires an interaction between pro-uPA and its cell surface receptor, uPAR. In agreement with this possibility, anti-uPAR antibodies (R3, R5) that prevent the pro-uPA/uPAR interaction also inhibit the effect of pro-uPA (FIG. 3). On the other hand the antibody R4, which does not interfere with pro-upA binding, has no effect. We conclude, therefore, that the inhibition of HIV-1 replication by pro-uPA requires an interaction with uPAR.

Figure 4:
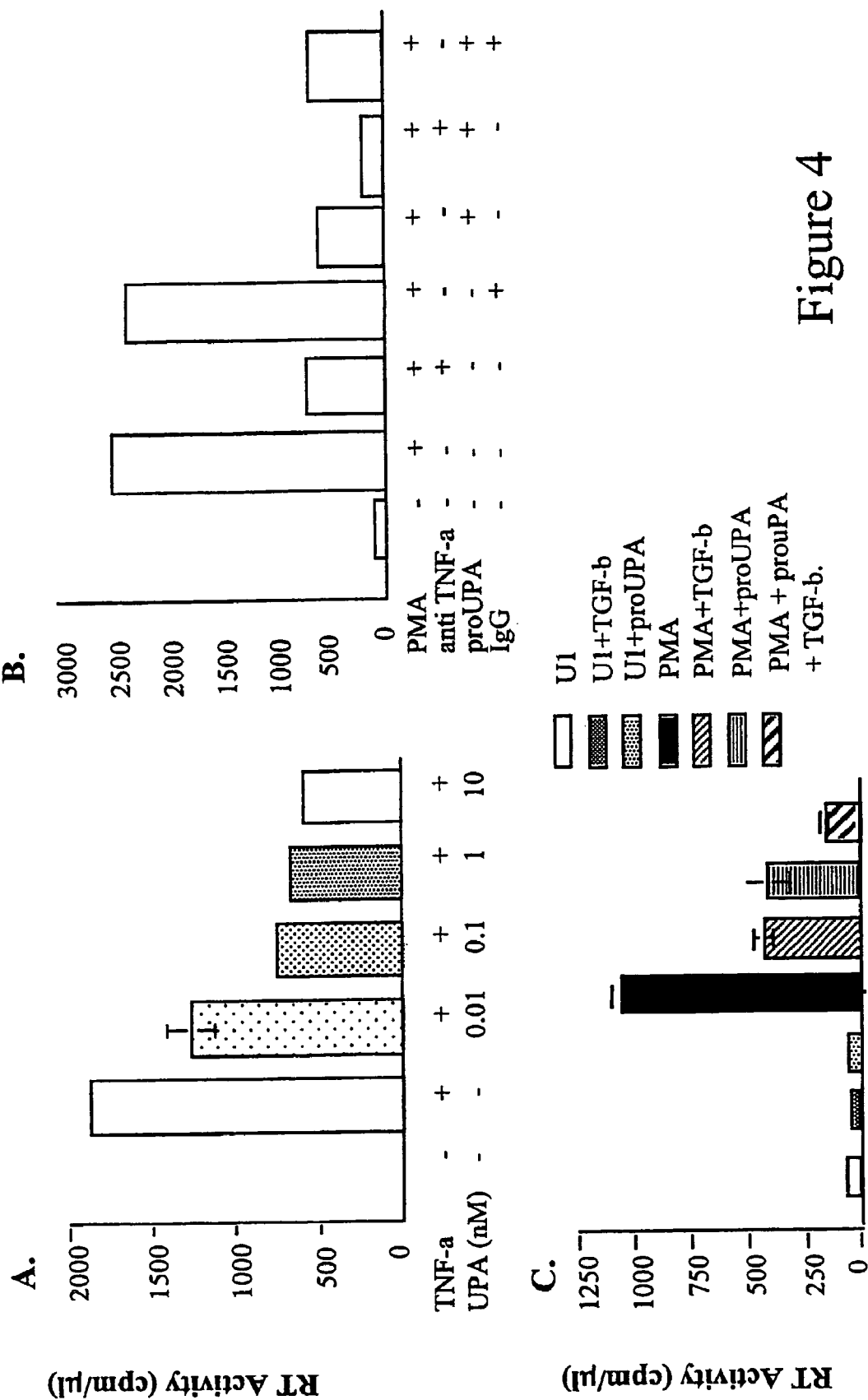
FIG. 4. —Pro-uPA inhibits TNF-alpha (1 ng/ml) induced reactivation of HIV-1 in U1 cells (A). Pro-uPA and anti-TNF-alpha antibodies (1 µg/ml) (B), or pro-uPA (10 nM) and TGF-beta (5 ng/ml) (C) synergize in inhibiting HIV-1 reactivation induced by PMA in U1 cells. Pro-uPA and all other effectors were added at zero time.

High levels of virus production can be obtained in U1 cells also by stimulation with the pro-inflammatory cytokines TNF-alpha and IL-6. These agents activate HIV-1 expression by activating transcription through NF-κB-dependent (TNF-alpha) or post-transcriptional mechanisms (IL-6) (Duh et al., 1989; Osborn et al., 1989; Poli et al., 1990). UPA (and pro-uPA) is also able to inhibit TNF-α-induced HIV replication (FIG. 4A). Since the effect of PMA on HIV-1 replication is in part dependent on the induction of TNF-alpha secretion, and hence partly inhibited by an anti-TNF-alpha antibody (Poli et al., 1990), one would expect the combination of the anti-TNF-alpha antibody with pro-uPA to be a more potent inhibitor of PMA-induced HIV-1 replication/expression. As shown in FIG. 4B, while anti-TNF-alpha and prou-uPA individually inhibit HIV-1 replication about 70%, together the reach a bigger effect, inhibiting by over 90%. This result suggests that pro-uPA and TNF-alpha act on a parallel signaling pathway.

TGF-β also inhibits PMA-induced HIV-1 replication/expression (Poli et al., 1991) in a NF-κB independent way. As shown in FIG. 4C, addition of the TGF-β and pro-uPA combination results in an additive inhibitory effect, about 90% inhibition with respect to the 60% obtained with only one reagent. These results therefore strongly indicate that pro-uPA interferes with a signaling step different from those activated by TGF-β φTNF-α and indicate that these steps are activated.

Figure 5:
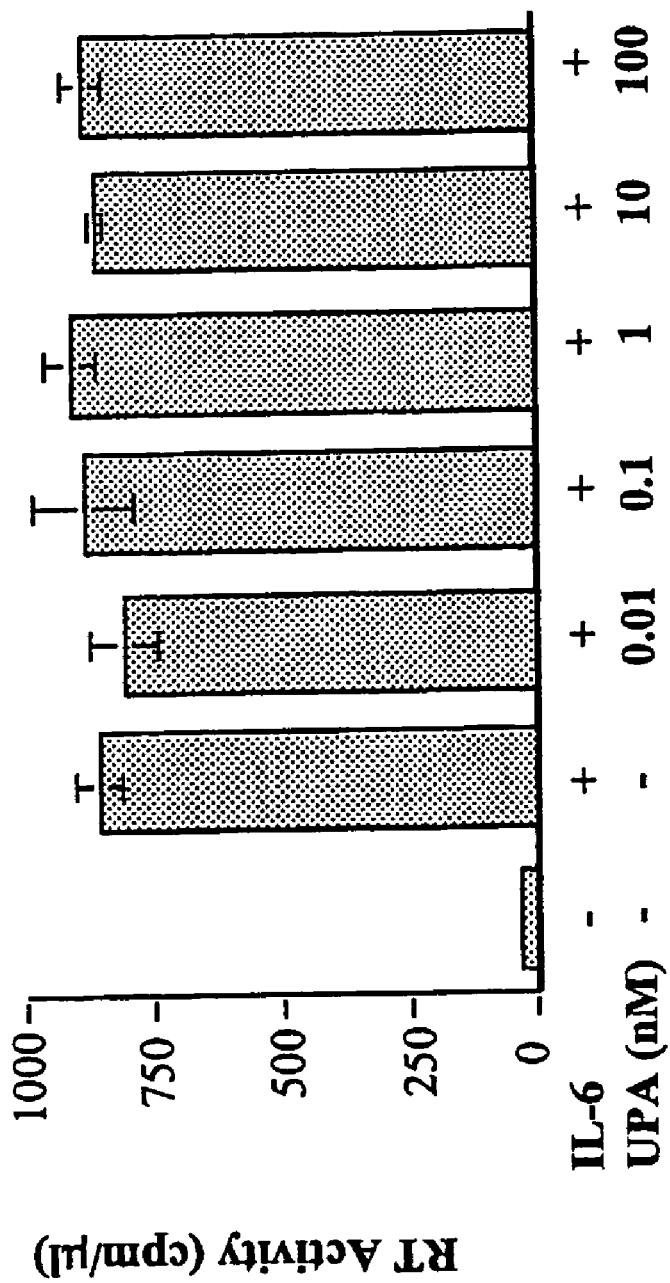
FIG. 5. —uPA does not inhibit IL-6 induced reactivation of HIV-1 in U1 cells. IL-6 was used at 10 ng/ml.

Unlike for PMA and TNF-α pro-uPA has no effect on the IL-6dependent HIV-1 replication in U1 cells (FIG. 5). Overall the results obtained with different citokines, suggest that pro-uPA acts by interfering with one specific signaling pathways that can lead to the inhibition of virus expression.

b. U1 cells express cell surface uPAR and shed it to the conditioned medium.

Since the inhibition by pro-uPA of HIV-1 replication requires an interaction with uPAR, we have tested whether U1 cells express uPAR. The test was performed by an immunoblot analysis of lysates of U1 cells, demonstrating the presence of a specific band reacting with anti-uPAR monoclonal antibodies. A similar analysis of the conditioned media shows the presence of uPAR in both untreated and PMA-treated U1 cells, in which uPAR is increased. Measurement of the amount of uPAR by ELISA gave essentially the same results (data not shown). These data are in agreement with previous reports showing that PMA can induce uPAR in U937 cells (Picone, 1989).

c. proUPA affects HIV-1 replications in primary cells.

Figure 6:
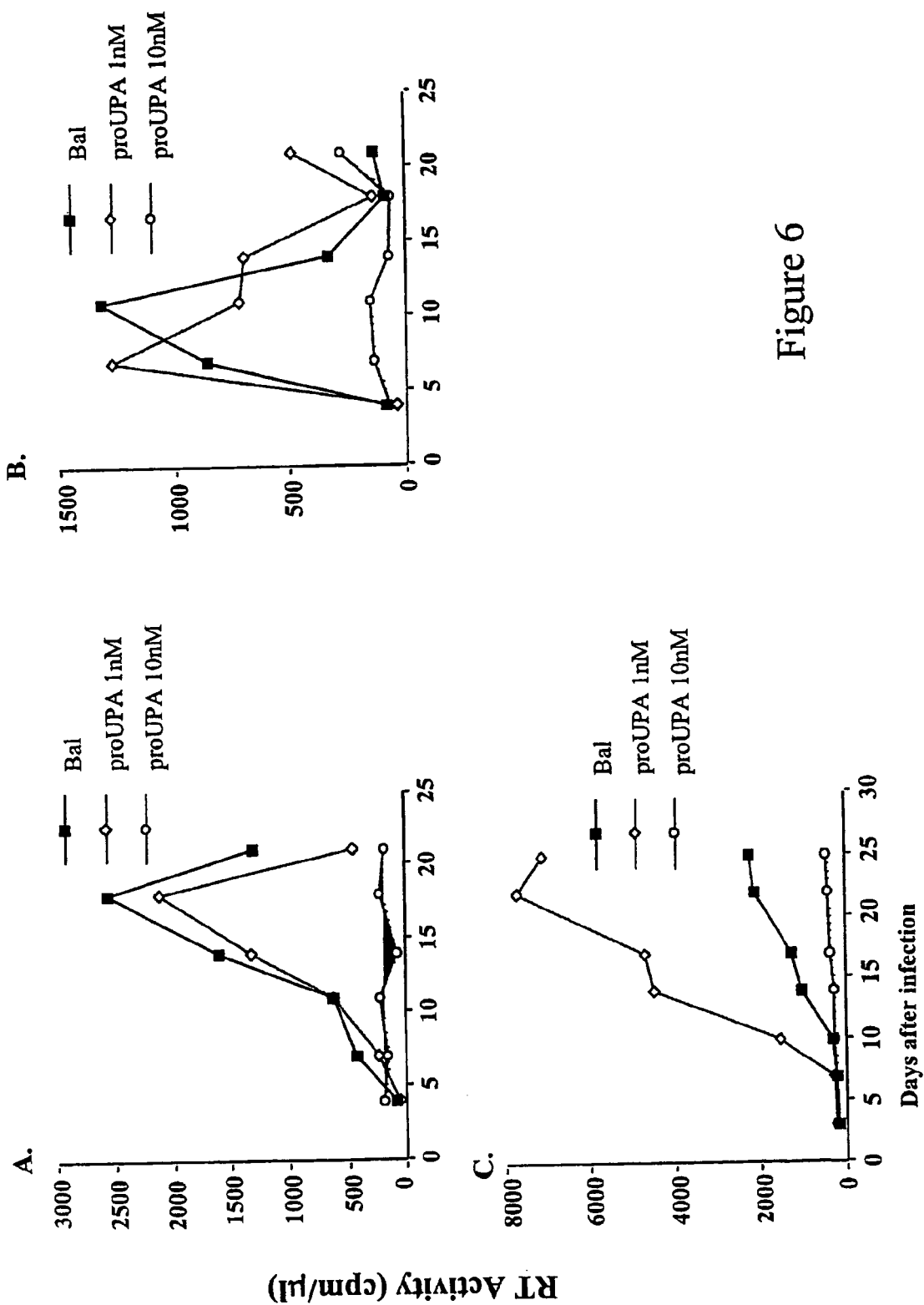
FIG. 6. —Pro-uPA has different effects on HIV-1 replication of human . . . (A), . . . (B) or . . . (C). The reverse transcriptase activity (RT, cpm/µl)) was measured every 3-4 days for a total of 20-25 days.
Figure 7:
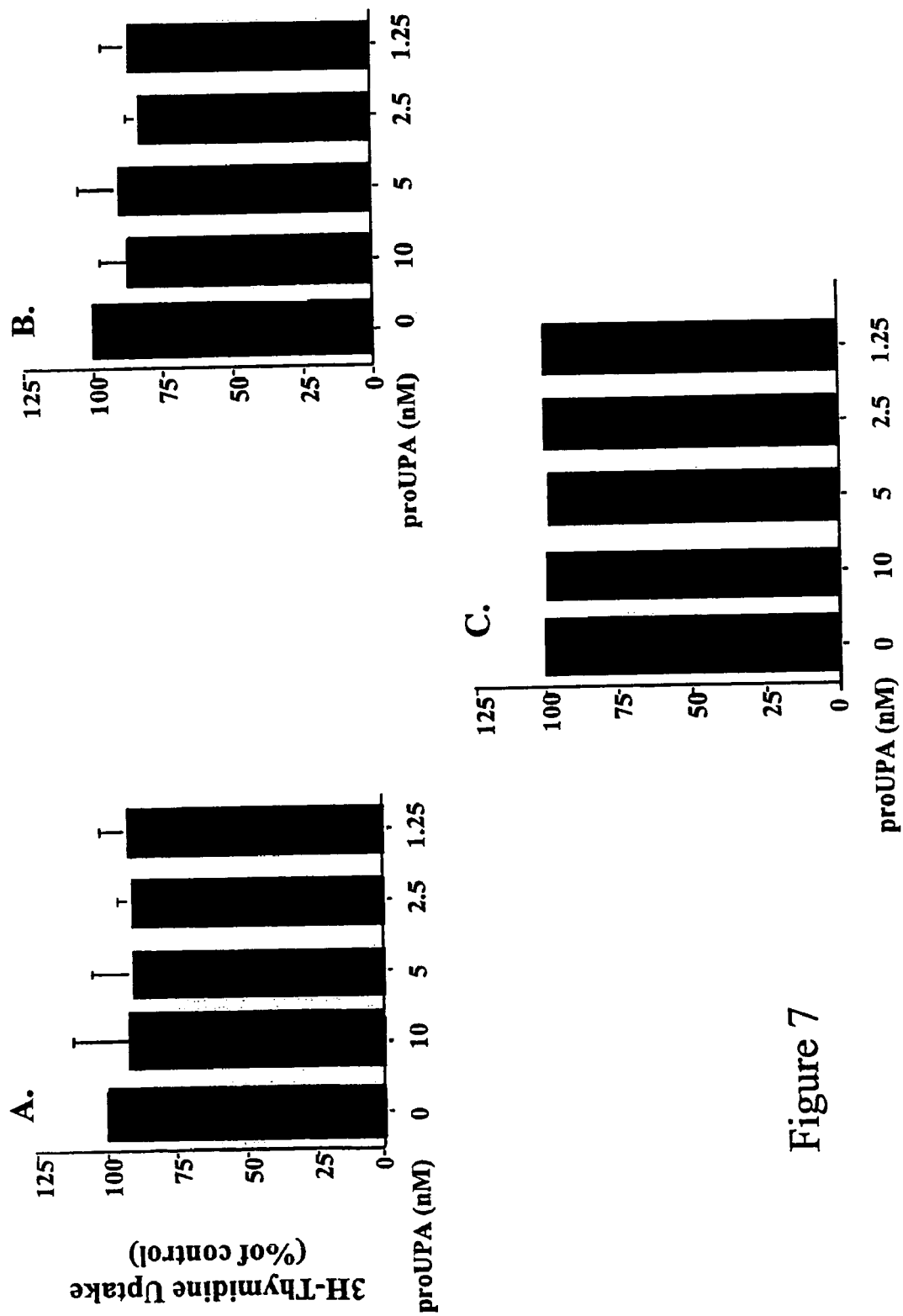
FIG. 7. —Pro-uPA has no effect on cellular thymidine incorporation (expressed in % of control, i.e. cells not receiving pro-uPA). The data are separated for . . . (A), . . . (B) or . . . (C).

When assayed on human peripheral blood monocytic cells (PBMC), pro-uPA was found to also affect the replication of HIV. However, qualitatively the effect of pro-uPA was shown to be dependent on its concentration and on the nature of the cells. In fact in the PHA-stimulated PBMC and IL-2 stimulated PBMC we found no effect of pro-uPA at 1 nM and a large inhibition of virus growth at 10 nM (FIGS. 6A and B). With monocytes derived macrophages, on the other hand, low concentrations of pro-uPA (10 nM) stimulated virus expression while higher concentrations inhibited it (FIG. 6C). Pro-uPA was not toxic to the cells: at 10 nM pro-uPA it showed essentially no effect on cellular proliferation as measured by $^3$H-thymidine uptake in uninfected PHA-stimulated PBMC, virus infected PHA-stimulated PBMC nor in uninfected resting PBMC (FIGS. 7A, B, C).

d. Correlation between viral replication and uPAR expression level.

Figure 8B:
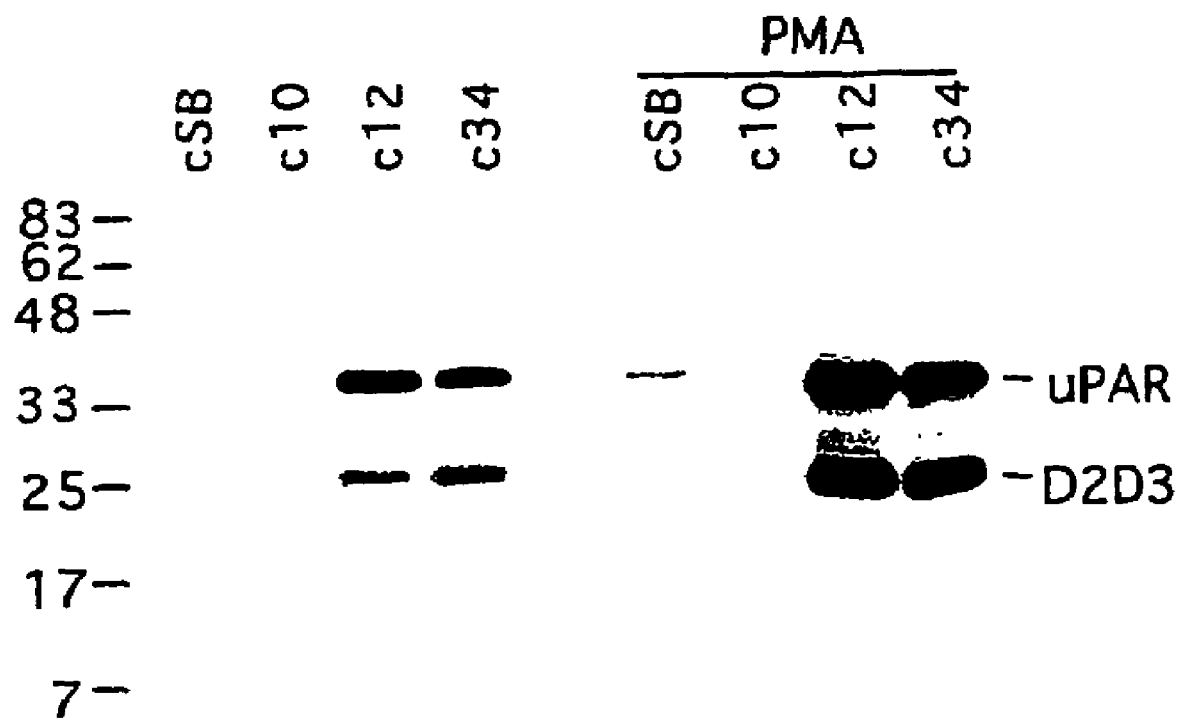
FIG. 8B. —Immuno-blot analysis of extracts of untreated or PMA-treated (10 nM) U937 cells clones. cSB and c10 are "plus" clones (high replication of HIV-1. c12 and c34 are "minus" clones (low replication efficiency).

We compared the levels of uPAR in various clones of U937 cells distinguished by their high ("plus" clones) or low efficiency ("minus" clones) in supporting HIV replication. FIG. 8A shows a correlation between the ability of HIV to replicate and the levels of uPAR measured by an ELISA. Non stimulated clones of U937 cells capable of sustaining productive HIV infection ("plus" clones: cSB and c10) expressed around 10-fold less uPAR than did U937 clones displaying delayed and/or reduced productive HIV infection ("minus" clones: c12 and c34). This difference was even bigger (around 30-fold) when cells were stimulated for 24 hours with PMA, since the "plus" clones were unable to up-regulate uPAR. FIG. 8B shows an additional approach to compare the levels of uPAR in the minus and plus clones, performed by immunoblotting of equal amounts of proteins from lysates of two clones each. This example clearly demonstrates that productive HIV infection of U937 cells inversely correlates with the expression level of uPAR. Indeed, cell clones able to sustain a high efficiency of viral replication have a very low uPAR level and do not even increase uPAR expression under conditions (treatment with PMA) in which uPAR is normally induced several fold in the same cell line (Picone, 1989).

EXAMPLE 2

Chemotaxis induced by uPA and "activated" uPAR fragments is mediated by the chemokine receptor FPRL1/LXA4R.

UPA and uPAR induce and are required for the chemotaxis of monocytes, THP-1 leukemic cells and several other cells. The derivative of uPA, ATF (amino terminal fragment), or the pro-enzyme pro-uPA have the same effect. In addition, the activated forms of uPAR (cleaved after residue 84) also activate chemotaxis. For all these stimulants, and in all cells tested, the mechanism remains the same (Degryse, 1999; Degryse, 2001; Fazioli, 1994; Resnati, 1996). In particular, these agents eventually rely on the activation of a transmembrane mediator. After binding to uPAR, uPA cleaves uPAR or modifies its conformation ("activation") to make it cleaved by between domain D1 and D2. The data show that the so-"activated" uPAR must interact with trans-membrane mediator that in turn transduces the migratory signals of pro-uPA/uPAR (Fazioli, 1994) (Blasi, 1997). This is due to the fact that uPAR is present on the outer cell surface and lacks an intracellular portion.

The chemotaxis by uPA and derivatives or by activated uPAR molecules (and the signaling pathway activated therefrom) is inhibited by pertussis toxin (Degryse, 1999; Degryse, 2001; Fazioli, 1994; Resnati, 1996). This is a property of G protein-coupled receptors, a family of proteins that include chemotactic receptors like chemokine receptors. The pertussis toxin sensitivity suggests therefore that the trans-membrane mediator (adapter) of the uPA/uPAR chemotaxis might be a G protein-coupled receptor.

Materials and Methods

Materials

Rabbit polyclonal antibodies specific for mouse uPAR were a kind gift of Dr. Gunilla Hoyer-Hansen and Prof. Keld Dano. The source of chemoattractacting agents has been described before (Blasi, 1997; Fazioli, 1997; Resnati, 1996).

Peptide 3 (AVTYSRSRYLEC [SEQ ID NO: 1] (Blasi, 1997) antiserum was prepared by chemical synthesis, coupling to keyhole limpet hemacyanin (KLH), and injection into rabbit using standard methods. The peptide-3 specific immunoglobulins were purified by affinity chromatography on peptide 3-Sepharose columns, by standard methods.

Cells

The THP-1 cells used in the present example have been previously described (Resnati, 1996). Human HEK293 cells were kindly donated by Dr. Hal Chapman and human HEK293/FPRL1 from Dr. J. M. Wang. HEK293 cells do not express uPA, pro-uPA or uPAR. They also do not express fMLP receptors, in particular FPRL1. HEK293/FPRL1 cells have been generated by transfection of FPRL1 cDNA in HEK293 cells (Murphy, 1996).

Chemotaxis

Chemotaxis assays were performed as described (Degryse, 1999) with modified Boyden chambers using filters (5 μm pore size, Corning) treated with collagen I (100 μg/ml) and fibronectin (10 μg/ml, Boehringer Mannheim). 20,000-40,000 cells in serum-free DMEM were added to the upper well while the chemoattractants were added to the lower well. When present, antibodies or desensitizing molecules were pre-incubated with the cells for one hour and were then added to both wells of Boyden chambers during the chemotaxis assay. Migration lasted for 60-120 in the case of THP-1 cells and 4-6 hours for the HEK293 or HEK293/FPRL1 cells. After migration at 37° C., cells remaining on the upper surface of filters were scraped off, the filters were fixed in methanol and stained in a solution of 10% (w/v) crystal violet in 20% (v/v) methanol. The experiments were performed in triplicate and the results presented represent the mean ±SD of the number of cells counted in ten high power fields per filter and are representative of at least three experiments. Random cell migration, i. e. migration in the absence of chemoattractant, was given the arbitrary value of 100%.

Cytofluorimetr

To test for the presence of various surface markers on different cells, we have employed cytofluorimetry. Antibodies recognizing specifically monocytes were directed versus CD14 (Pharmingen, Calif., U.S.A.). R2 monoclonal antibody was used for uPAR (Rønne, 1991) and the anti-FPRL1 antibody (Fiore, 1995) was obtained from Dr. Mario Romano.

Isolation of Mouse Peritoneal Macrophages

Murine macrophages were isolated by repeated washes of the peritoneal cavity of euthanized mice, with Dulbecco minimum essential medium (DMEM) supplemented with 5% FBS. To increase the efficiency of recovery, mice were injected with. 1 ml of 3% Thioglycollate, and macrophages collected 3-5 days later. The purity of the preparation was determined by flow cytometry analyses with anti-MAC-1 monoclonal antibodies.

Immunoblotting Analysis

Total cell extracts in PBS 1%-Triton X100 were incubated at 95° C. for 3 min. in 0.5% SDS and 2 mM DTT in a final volume of 10 μl. Proteins were deglycosilated (Behrendt, 1991; Sidenius, 2001) by addition of deglycosilation buffer (PBS containing 0.5% Triton X100 and 15 mM EDTA), 1 unit of peptide-N-glycosidase F (PNGase-F) and incubation at 37° C. overnight. For Western blotting the samples were run on 12% SDS-PAGE gels under reducing conditions, blotted onto a PVDF membrane and reacted with horse radish peroxidase-conjugated anti-rabbit IgG. Positive staining was revealed with Super Signal West Dura Extended Duration Substrate from Pierce Chem. Co. The rabbit polyclonal antibody directed against the murine uPAR was used at 1 μg/ml for the western blotting analysis.

Results

4. The chemotactic epitope of UPAR is essential in promoting THP-1 chemotaxis.

Figure 9:
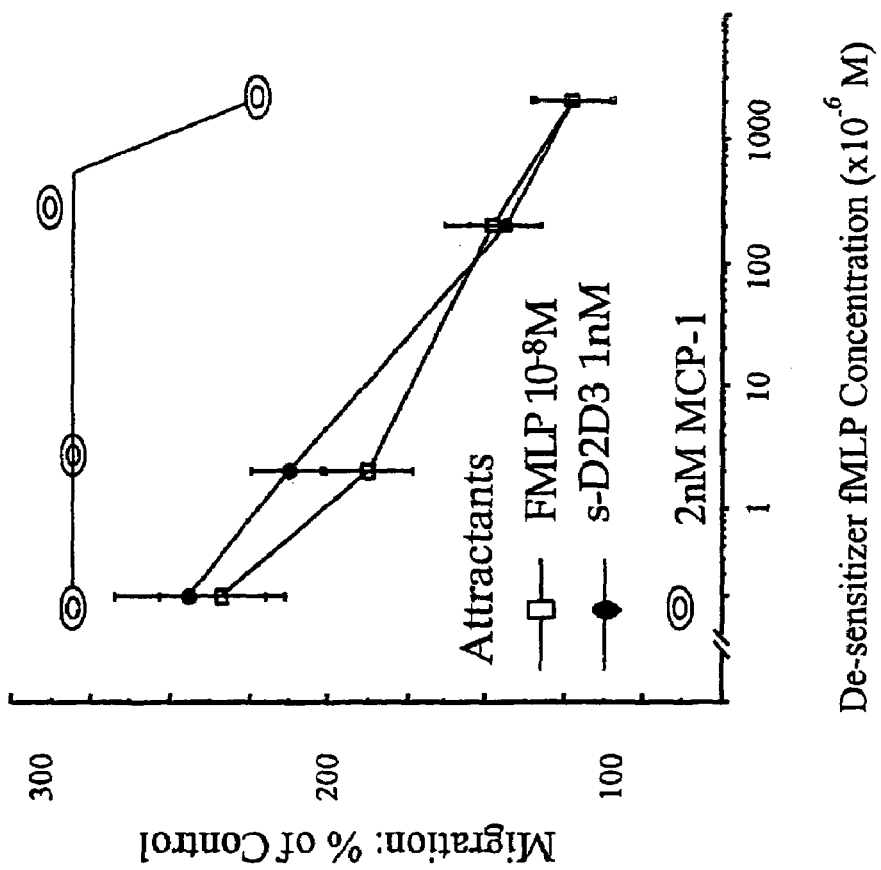
FIG. 9: —Identification of the uPAR adapter. A. Effect of the antibody vs. peptide 3 (dilution 1 to 100) on the migration promoted by D2D3$_{88-278}$ in human THP-1 cells. B. Desensitization experiments with fMLP. Chemoattractants were used at the indicated concentrations.
Figure 9:
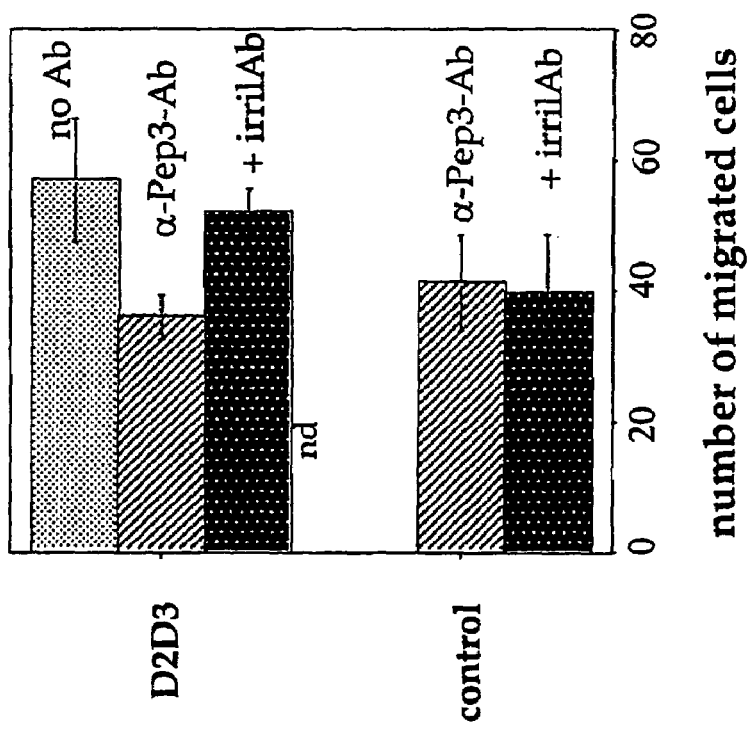

In order to test whether chemotaxis by uPA/ATF/pro-uPA and by "activated" uPAR really depends on the chemotactic epitope identified in the linker region between domain D1 and D2 (Blasi, 1997; Fazioli, 1994), we have generated an antibody to the synthetic peptide AVTYSRSRYLEC [SEQ ID NO: 1], and tested peptide-specific IgG in chemotaxis experiments with THP-1 cells. As shown in FIG. 9A, ATF induced chemotaxis in THP-1 cells in the presence of irrelevant antibodies. However the effect was strongly reduced in the presence of 10 μg/mL anti-peptide 3 lgG. This experiment shows that a reagent that specifically interferes with the chemotactic epitope of uPAR can inhibit uPA-uPAR dependent cell migration, even though it does not prevent the binding of uPA to uPAR.

5. Desensitization experiments.

Chemoattractants can de-sensitize each other by occupying the binding site of a G-protein coupled receptors. Alternatively, they also act indirectly by inducing the phosphorylation of other receptors. To identify the trans-membrane adapter mediating the uPA/uPAR chemotaxis, we have exploited the property of desensitization and have looked for a chemoattractant able to de-sensitize cells monocytes or THP-1 cells from uPA.

To induce chemotaxis in a uPA/uPAR-dependent way, we have employed in this example $D2D3_{88-279}$, a chymotrypsin-cleaved, soluble, purified form of uPAR endowed with potent chemotactic activity (Resnati, 1996). As a de-sensitizing chemokine, we have used the bacterial formylated peptide fMLP (formyl-methionyl-leucyl-phenylalanine). As shown in FIG. 9B, fMLP de-sensitizes THP-1 cells from $D2D3_{88-279}$ inhibiting chemotaxis by 50% at around 10-20 μM. However, de-sensitization is specific for $D2D3_{88-279}$ since fMLP did not affect MCP-1 chemnotaxis except marginally at very high concentrations (200 μM).

The chemokine fMLP activates chemotaxis through two different receptors: a low affinity receptor FPRL1 (also called LXA4R), and an high affinity receptor, FPR. Since fMLP de-sensitized against $D2D3_{88-279}$ and ATF at 20 μM, the receptor involved in the desensitization of chemotaxis by $D2D3_{88-279}$ must be FPRL1/LXA4R and not FPR.

6. Transfection of the FPRL1 cDNA in cells not responding to $D2D3_{88-279}$ confers $D2D3_{88-279}$ responsiveness.

Figure 10:
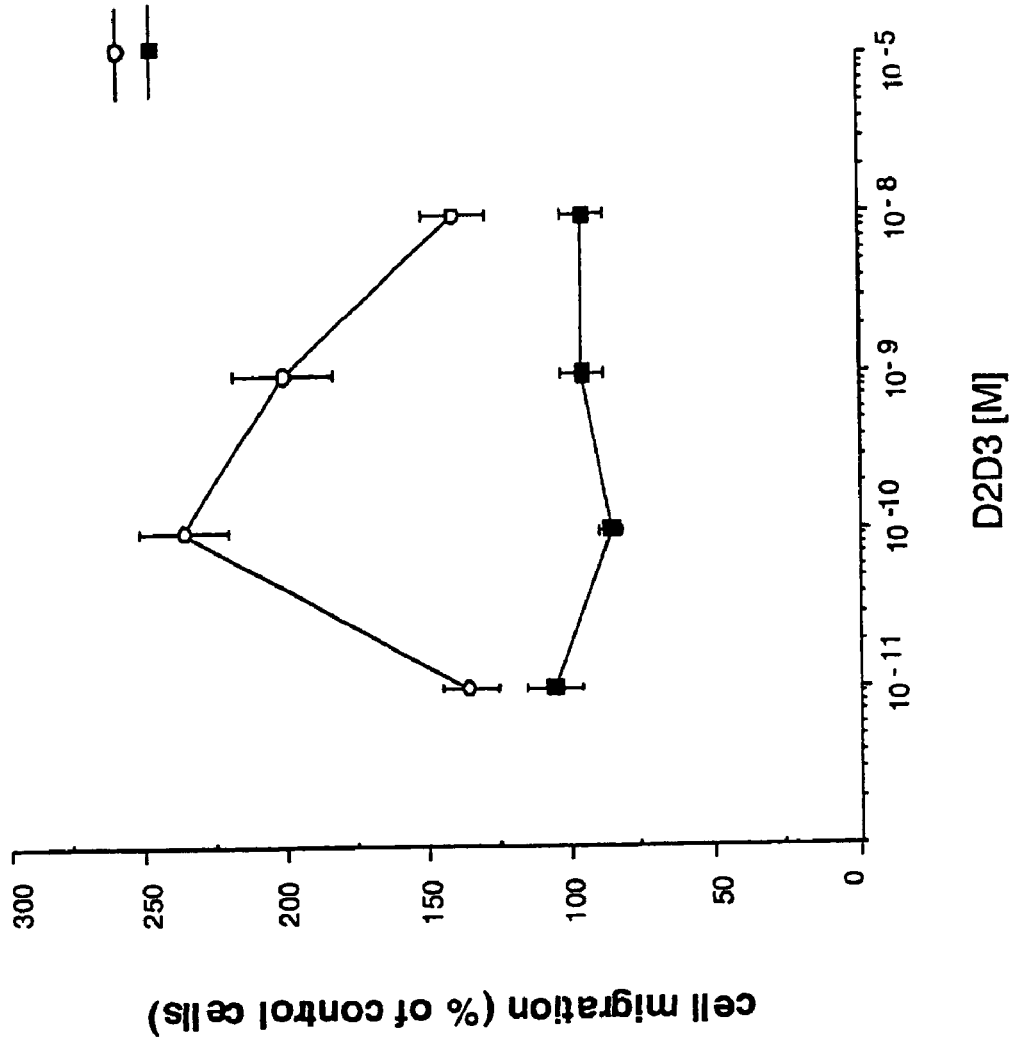
FIG. 10. —D2D3 stimulates chemotaxis of HEK293 only when they are transfected with the FPRL1/LXA4R cDNA. D2D3$_{88-278}$ was obtained by cleavage of full length suPAR with chymotrypsin, and purification of the fragment.

In order to positively prove that any given molecule mediates the signaling by uPA/uPAR, it would be advantageous to have available a cell line not expressing uPA, uPAR nor the mediator itself, and hence not responding to the chemotactic stimuli of either uPA/pro-uPA/ATF or of activated uPAR. We found that the HEK293 cells do not express uPA nor uPAR and do not respond to uPA/ATF nor to $D2D3_{88-279}$ (FIG. 10). We have therefore compared the effect of $D2D3_{88-279}$ on HEK293 vs. HEK293 cells transfected with FPRL1/LXA4R. As shown in FIG. 10, HEK293 do not respond to $D2D3_{88-279}$ in chemotaxis. However, HEK293 transfected with FPRL1/LXA4R respond well with a maximum at about 0.1 nM D2D3 $_{88-279}$. This result indicates that transfection of HEK293 cells with the FPRL1 cDNA is sufficient to confer the uPAR-responsiveness.

7. Mouse macrophages lacking the uPA gene do not cleave uPAR

Figure 11:
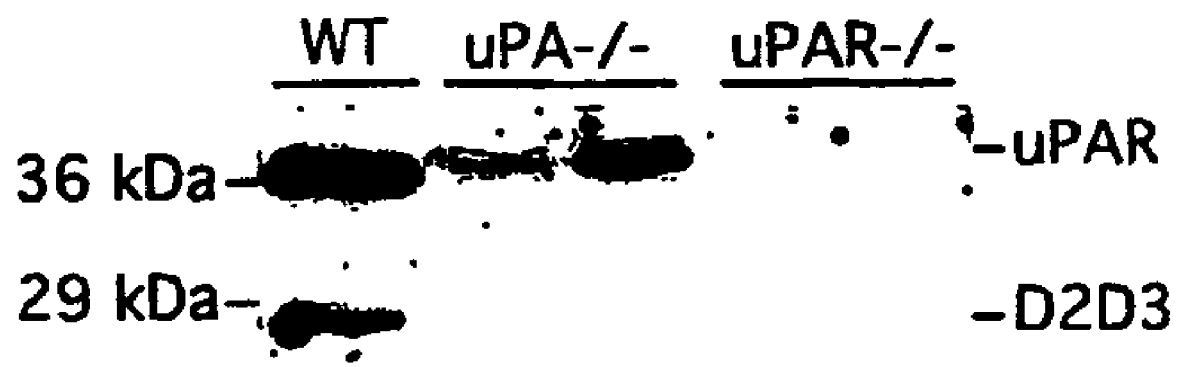
FIG. 11. —Immuno-blotting analysis of murine uPAR. In peritoneal macrophages of wt mice (lane 1), uPAR is present in the full length (36 kD) and in the cleaved D2D3 form (26 kD). In uPA-deficient mice (lanes 2 and 3), the 26 kD form is missing. The absence of bands in the macrophages of uPAR-deficient mice (lanes 4 and 5) demonstrates the specificity of the antibodies.
Figure 12:
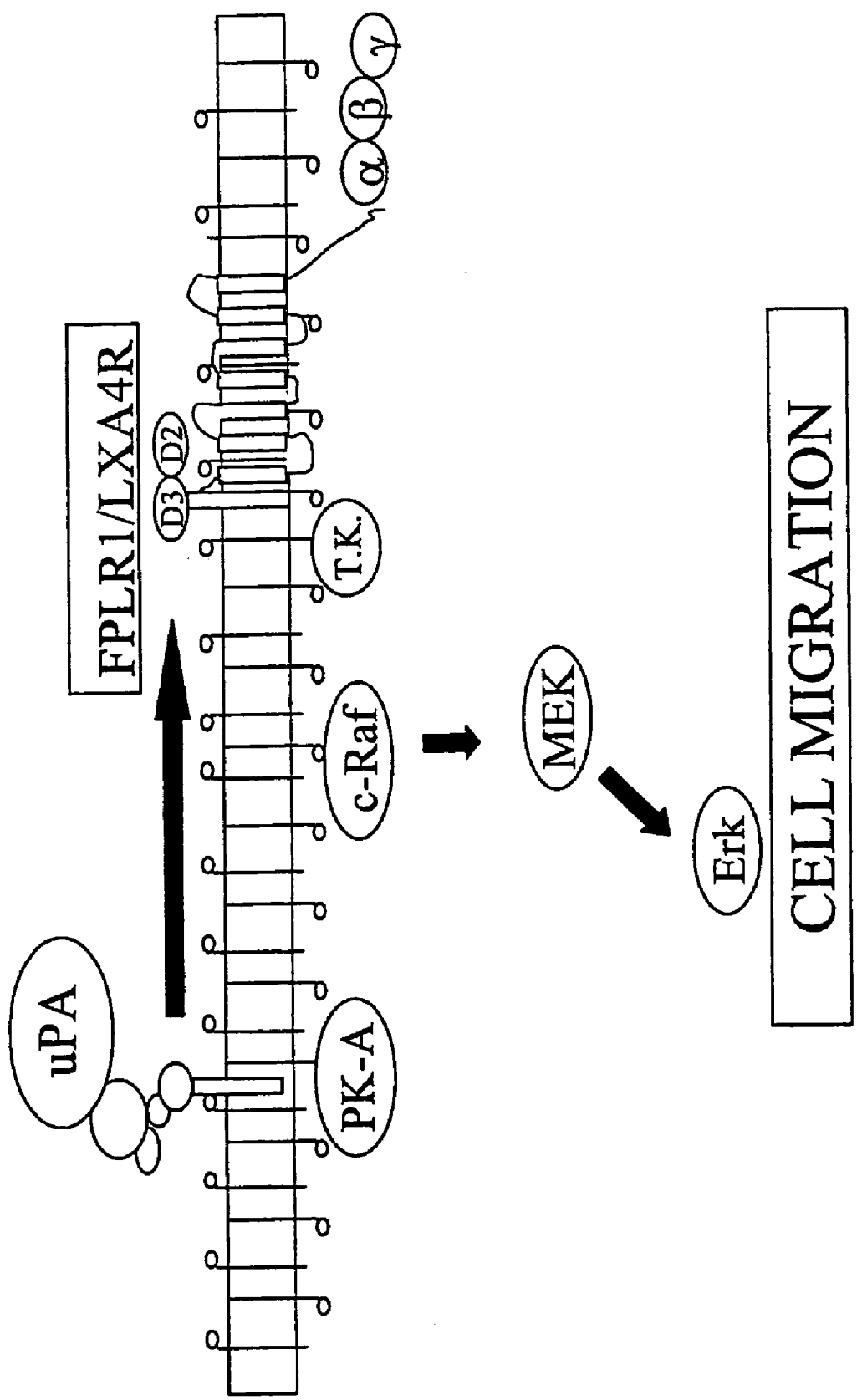
FIG. 12. —Scheme of activation of migration through uPA/uPAR. uPA binds to uPAR and cleaves it at the D1-D2 linker region. The "activated" uPAR then binds the FPLR1/LXA4R which transduces intracellularly its migratory signal.

Mice which are genetically uPA-deficient are also immuno-deficient because their macrophages and T-lymphocytes are unable to migrate to the sites of infection (Gyetko, 1996). The same effect is observed in the uPAR-deficient mice (Gyetko, 2000). The migration-deficiency of the uPA-null mice might be due to the inability of the cells of these mice to cleave (activate) surface uPAR, because of the lack of uPA. If this were the case, one would expect uPAR to be found intact in the cells of a uPA k.o. mouse. FIG. 11 shows an SDS-PAGE and immuno-blotting analysis with specific rabbit polyclonal antibodies directed to murine UPAR, in which lysates (in duplicates) of thioglycollate-elicited peritoneal macrophages from wt, uPA$^{-/-}$ and uPAR$^{-/-}$ are compared. The extracts were first de-glycosylated and subsequently run on SDS-PAGE, blotted on PVDF filters and challenged with the anti-mouse UPAR antibodies. As shown in FIG. 11, the extract from peritoneal macrophages of wt mice (lane 1) shows two specific bands, 35 and 25 kD respectively, when blotted with the anti-mouse uPAR antibody. These correspond to the molecular weights expected for human full length and D2D3 uPAR (Behrendt, 1991; Sidenius, 2000), and therefore are likely to correspond to the same species in mouse (lanes 2,3). On the contrary, extracts from uPA$^{-/-}$ macrophages only show the upper band, i.e. full length uPAR. The absence of the bands in uPAR$^{-/-}$ macrophages extracts (lanes 4,5) demonstrates the specificity of the natibodies. The data therefore show that a fragment corresponding to the size of a $D2D3_{84-278}$ does not accumulate in uPA$^{-/-}$ mice, and hence that the cleavage between domain D1 and D2 may not occur in uPA$^{-/-}$ mice. The mmobility of this fragment is identical to that observed in human cells, and which has been identified as $D2D3_{84-278}$ by amino acids sequencing (Hoyer-Hansen, 1992; Solberg, 1994). This result correlates with the deficient cell migration in uPA$^{-/-}$ mice (Gyetko, 1996) and therefore agrees with the hypothesis that in vivo uPAR cleavage is required for cell migration. The data also indicate that uPA directly cleaves uPAR. However, it is still possible that cleavage be due to a different protease that however requires uPA for activation. Indeed, activation of MMP-2 and MMP-9 is deficient in uPA$^{-/-}$ mice (Carmeliet, 1997). We therefore hypothesize that the migration of T lymphocytes and monocytes/macrophages to sites of infection requires cleavage of uPAR by uPA, and that the activated uPAR in turn binds to and stimulates the FPRL1-LXA4R chemotactic receptor. A scheme recapitulating the mechanism is shown in (FIG. 12).

EXAMPLE 3

Inhibition of uPA/ATF/uPAR chemotaxis by anti-FPLR1/LXA4R reagents.

The specific response of FPRL1/LXA4R containing cells to $D2D3_{84-278}$ (FIG. 10) strongly suggests that the G-proteincoupled FPRL1/LXA4R receptor is the mediator of uPA and "activated" uPAR-induced chemotaxis. To substantiate this hypothesis, we have used cells that contain several chemokine receptors, including FPRL1/LXA4R, and have tested whether specific antibodies to FPRL1/LXA4R inhibit ATF or $D2D3_{84-278}$ induced chemotaxis.

Materials and Methods

Materials

The anti-LXA4R/FPRL1 antibodies (Fiore, 1995) were a generous gift of Dr. Mario Romano (Chieti, Italy) and Clarles Serhan (Boston, Mass., USA).

Cells

THP-1 cells have been described before (Resnati, 1996). Monocytes were obtained by two rounds of centrifugation over Ficoll (1.077 g/l) and Percoll (Pharmacia Biotech.) gradients from peripheral blood of healthy volunteers. Briefly, heparinized blood was diluted 1:1 with PBS and 3 ml of Ficoll-Hypaque were layered underneath 10 ml of blood/PBS mixture. Upon centrifugation, the mononuclear cell layer was recovered, the cells were washed to remove any contaminating Ficoll, and monocytes were purified by Percoll gradients. The purity of the separated populations was determined by flow cytometry analyses with anti-CD14 monoclonal antibodies.

Results

Human peripheral blood monocytes (PBM) and the leukemic monocytic THP-1 cell line express several chemokine receptors including the fMLP receptors FPR and FPRL1, but also respond to $D2D3_{88-279}$ in chemotaxis. PBM and THP-1 cells also express several other chemokine receptors, which include receptors that respond to the monocytes chemotactic protein-1 (MCP-1), a receptor distinct from that of other chemokines, like fMLP (results not shown as reproducing data present in the literature). Cytofluorimetry shows that the employed cells indeed express uPAR and FPRL1 (not shown).

Figure 13:
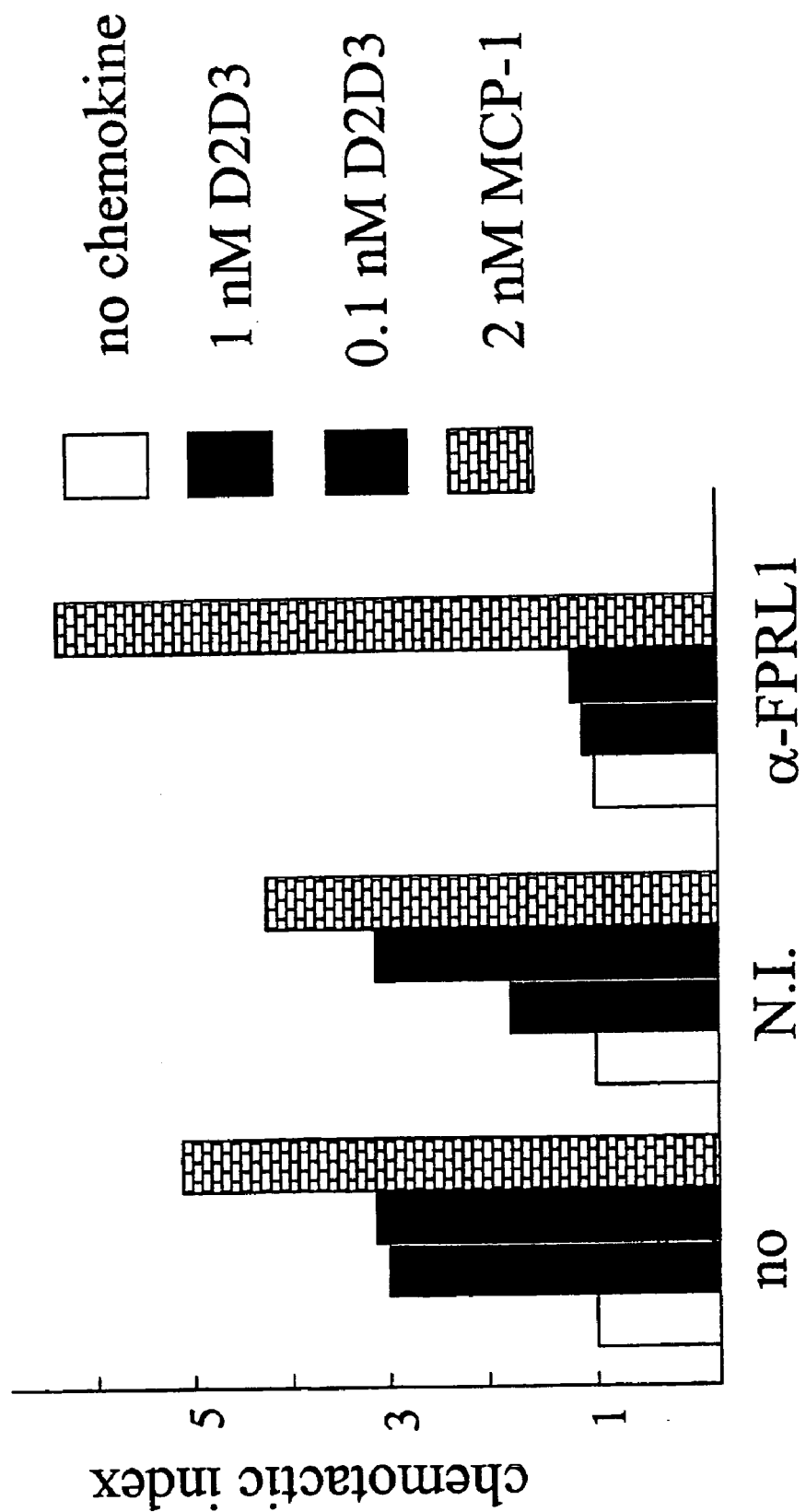
FIG. 13. —D2D3-induced chemotaxis in monocytes is specifically blocked by anti-bodies specifically recognizing FPRL1/LXA4R. Human peripheral blood monocytes were stimulated with none, or with D2D3$_{88-278}$ at two concentrations or MCP-1 at 2 nM (see scheme). no=no antibodies. N.I.=non immune serum. α-FPRL1=anti-FPRL1 antibodies.

As shown in FIG. 13, both MCP-1 and $D2D3_{88-279}$ induce chemotaxis of fresh human monocytes. The activity of $D2D3_{88-279}$ is specifically blocked by anti-FPRL1/LXA4R antibody; however, the antibody has no effect on MCP-1. Thus the FPRL1 receptor is necessary to mediate uPAR-dependent chemotaxis.

As shown in FIG. 14, the amino terminal moiety of uPA, ATF, as well as MCP-1 induce chemotaxis in THP-1 cells, as previously reported (Resnati, 1996). Also in this case, the FPRL1/LXA4R antibody specifically blocked ATF chemotaxis, while having no effect on MCP-1 chemotaxis.

EXAMPLE 4

Specific antibodies to detect and quantitate "activated" uPAR fragments.

The chemotactic $D2D3_{88-279}$ fragment of uPAR is generated in vitro by cleavage with chymotrypsin of a soluble form of uPAR (Fazioli, 1997) (see FIG. 1). A form of uPAR containing domains D2 and D3 and starting at residue 84 has been identified in vivo: in vitro, uPA itself at physiological concentrations cleaves suPAR and cell surface uPAR at residue 84 (Hoyer-Hansen, 1997; Hoyer-Hansen, 1992; Sidenius, 2000). In addition, the synthetic uPAR peptide with the highest chemotactic activity encompasses residues 84-97 (Fazioli, 1997). It is possible therefore that the activation of uPAR in tissues is due to cleavage by uPA. Finally, the failure of uPA-deficient mice to cleave uPAR (see FIG. 11) suggests that the migration-defective phenotype is due to the lack of cleavage.

Since uPAR cleavage can "activate" uPAR conferring a migration-promoting phenotype, cleavage of uPAR therefore must confer an "inflammatory" phenotype to cells. However, cleavage in the linker region between domain D1 and D2 would have very different effects depending on where the cleavage occurs. For example, cleavage between residues 84 to 89 would generate an "activated" uPAR, while cleavage between residue 89 through 93 would destroy the activity. This is based on the finding that while peptides AVTYSRSRYLEC [SEQ ID NO: 1] and SRSRY [SEQ ID NO: 2] are active in chemotaxis-promotion, cleavage of the AVTYSRSRYLEC [SEQ ID NO: 1] peptide with plasmin (which cleave immediately after the two arginine residues) destroyed the activity (data not shown). Clearly, the detection of the presence of "activated" uPAR and its quantitative measurement (in blood, urine, cells or tissue fragments) with a simple assay would be useful in evaluating the inflammatory state of an individual. However, current methods do not allow an easy evaluation of where uPAR is cleaved as they require protein purification and sequencing.

Antibodies, however, can discriminate between very similar amino acids sequences or even sequences differing by one single residue. We have searched, therefore, for antibodies specific for "activated" uPAR fragments.

Materials and Methods

Preparation of Peptide 3 Antiserum

Peptide 3 (AVTYSRSRYLEC [SEQ ID NO: 1]) (Blasi, 1997) was synthesized, coupled to keyhole limpet hemacyanin (KLH), and a rabbit antiserum generated by standard methods. The peptide-3 specific immunoglobulins were purified by affinity chromatography on peptide 3-Sepharose columns, by standard methods.

Expression and Purification of Recombinant uPAR and uPAR Fragments

Full-length soluble uPAR (suPAR) was expressed in CHO cells stably transfected with a cDNA encoding aminoacid 1-278 of mature human uPAR and purified by affinity-chromatography on a column with R2 monoclonal antibody immobilized on CNBr activated Sepharose (Pharmacia) as described (Blasi, 1997; Fazioli, 1997). We have also employed similar recombinant fragments containing at their carboxy terminus the FLAG epitope (Prickett, 1989). $D2D3_{88-278}$ and $D2D3_{87-278}$ were prepared by hydrolysis of full-length suPAR with chymotrypsin and MMP-12, respectively, followed by purification of the D2D3 moiety on the same column as described above. The recombinant proteins $D2D3_{84-278/FLAG}$ and $D^2D3_{92-278/FLAG}$ were purified from the conditioned medium of transiently transfected COS7 cells and purified on a M2-affinity column (Sigma) according to the manufactures instruction.

Western Blotting Assays 10 ng of purified suPAR, $D2D3_{88-278}$, $D2D3_{84-278/FLAG}$ and $D^2D3_{92-278/FLAG}$ proteins were denatured under lightly reducing conditions and enzymatically deglycosylated using PNGase F (Boehringer) as described elsewhere (Dano, 1990). The deglycosylated proteins were separated by 15% SDS-PAGE and transferred to PVDF membranes using semi-dry electro transfer. After blocking in 5% non-fat dry milk, blots were incubated with 0.5 µg/ml of a polyclonal anti-uPAR antibody recognizing all known forms of uPAR or with a 1:2000 dilution of the anti-Pep3 serum. The blots were washed, incubated with a secondary horse-radish peroxidase conjugated donkey-anti-rabbit antibody (1:5000, Amersham), washed, and developed using a chemoluminescent substrate (SuperSignal Dura, Pierce).

ELISA Assay

NUNC maxisorb 96-well plates were coated ON with 1 µg/ml R2 antibody diluted in coating buffer (0.1 M NaHPO4, pH 9.6). The plates were washed three times with PBS-T (PBS containing 0.1% Tween 20) and blocked for one hour at 37° C. with 2% BSA in PBS. Separate wells were incubated with the recombinant purified suPAR and D2D3 fragments generated by cleavage with chymotrypsin or MMP-12, and diluted to 10 ng/ml in dilution buffer (PBS containing 1% BSA). After incubation at 37° C. for one hour the plates were washed and incubated for one hour at 37° C. with either a polyclonal anti-uPAR antibody recognizing all forms of uPAR or the affinity purified anti-peptide 3 antibody, both diluted to 1 µg/ml in dilution buffer. After additional washing the plates were probed for one hour at 37° C. with alkaline phosphatase conjugated mouse-anti-rabbit antibody (1:1000 Sigma), washed and developed with a chromogenic alkaline phosphatase substrate (pNPP, Sigma) as recommended by the manufacturer. Specific binding was determined by subtracting the absorbance observed in well receiving no suPAR or surAR fragments. The data are presented as the average (+/−SD) of a duplicate determination.

Results

Figure 15:
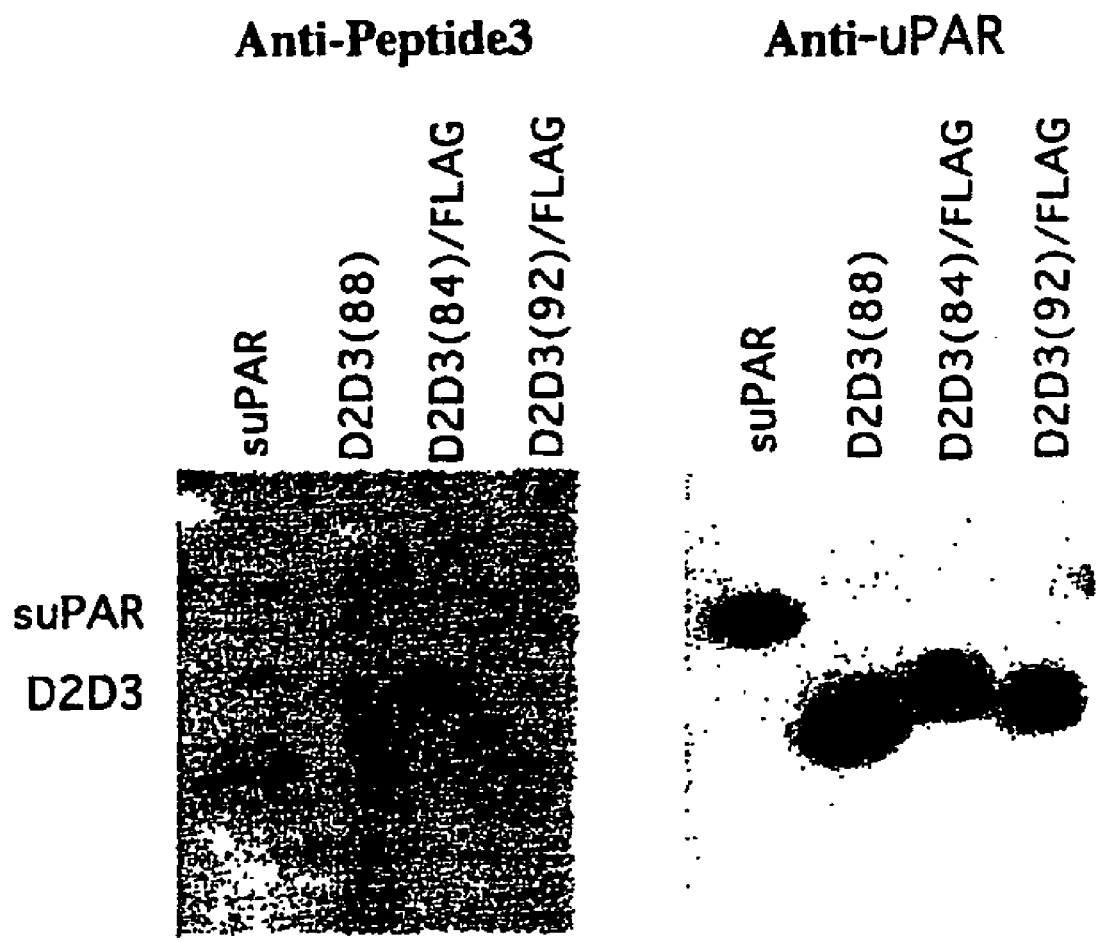
FIG. 15. —Use of the anti-peptide 3 antibody to identify specifically activated uPAR fragments. Full-length human suPAR and D2D3 fragments with different amino termini were run in SDS-PAGE, blotted and tested with two different antisera. D2D3(88) is the fragment generated by cleavage of suPAR with chymotrypsin. D2D3(84)FLAG and D2D3(92)FLAG have been generated by recombinant DNA technology and also contain a carboxy-terminal FLAG epitope.

To determine the, specificity of the Peptide3 antibody, western blotting experiments were performed on suPAR and D2D3 fragments carrying different well-defined parts of the uPAR linker region. When blots were probed with the anti-Peptide3 antibody the $D2D3_{84-278/FLAG}$, but not the suPAR, $D2D3_{88-278}$, or $D2D3_{92-278/FLAG}$ proteins, was efficiently recognized (FIG. 15, left panel). This was not caused by different loading of the proteins on the gel as all recombinant proteins were equally well recognized by a polyclonal antibody directed against intact suPAR (FIG. 15, right panel). Surprisingly, the anti-Peptide 3 antibody did not recognize intact suPAR (which obviously carries the entire linker region). This experiment demonstrates that the anti-peptide 3 antibody preferentially recognizes cleaved uPAR and that the epitope(s) recognized includes one or more of the aminoacids Ala84-Tyr87. It also suggests that the sequence 85-87 is buried in the intact uPAR and becomes exposed when uPAR is cleaved.

Figure 16:
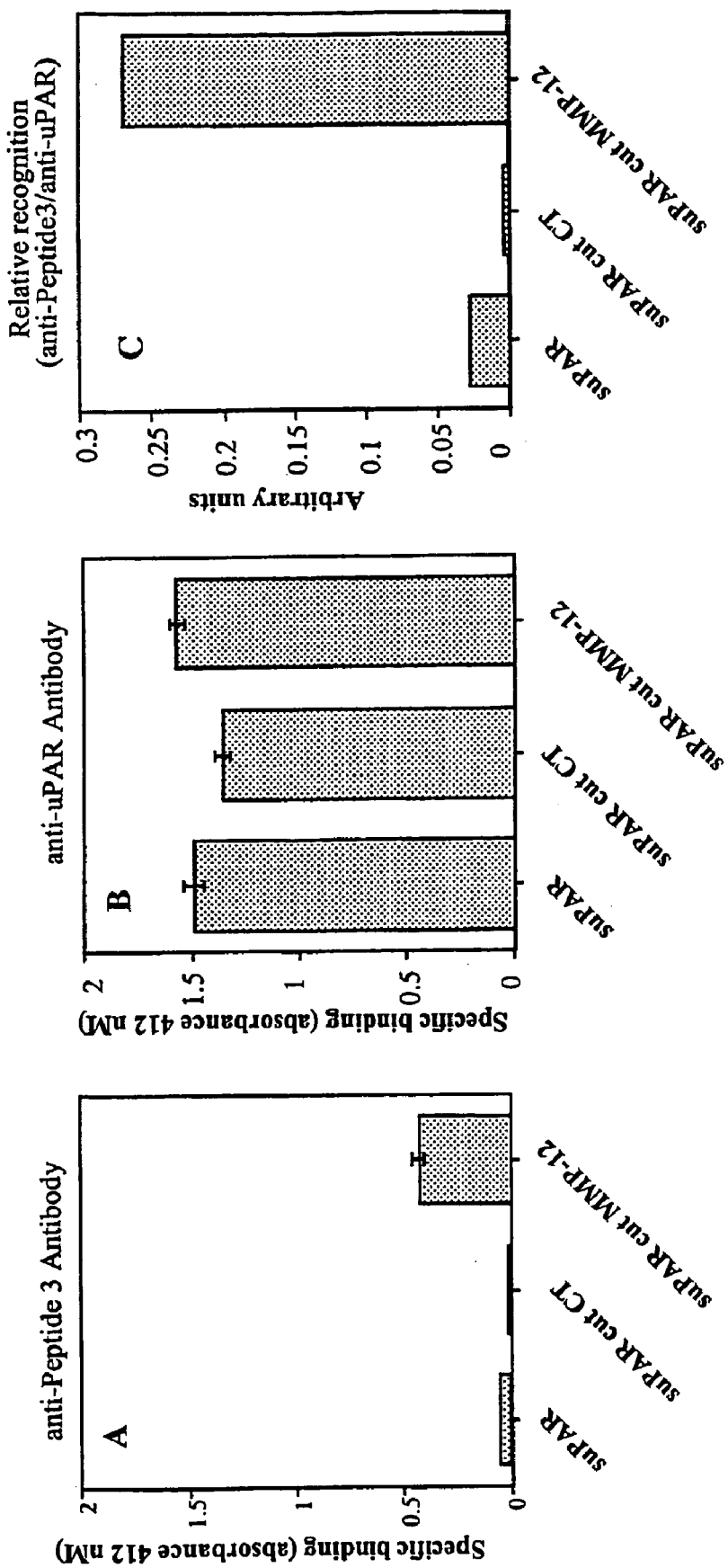
FIG. 16. —Enzyme-linked ImmunoSorbent Assay (ELISA) of suPAR and D2D3 fragments with different amino termini. SuPARcutCT is a D2D3 preparation obtained by cleavage of suPAR with chymotrypsin and purification (i.e. amino terminus at residue 89). suPARcutMMP12 isa D2D3 fragment obtained by cleavage with MMP-12 and purification.

These observations were confirmed using an independent in vitro binding (ELISA) experiment. In this assay suPAR and the different D2D3 proteins are first captured using a monoclonal antibody (R2, which recognizes the carboxy termini of all suPAR forms, cleaved by a protease in vitro) previously adsorbed to plastic. In a second step the bound proteins were probed with the polyclonal (rabbit) antiserum directed against Peptide 3 or against intact uPAR. The bound rabbit antibodies were quantified using anti-rabbit enzyme-conjugated secondary antibody and a colorimetric detection. While the anti-uPAR antiserum recognized equally suPAR, chymotrypsin-cleaved suPAR and MMP-12-cleaved suPAR (FIG. 16, panel B), the anti-peptide-3 IgG only recognized an MMP-12-cleaved suPAR (FIG. 16, panel A). Chymotrypsin cleaves uPAR at residue 87-88 (Behrendt, 1991), while MMP-12 cleaves at residue 86/87 (data not shown). Therefore, the anti-peptide 3 IgG specifically recognize D2D3 fragments whose amino terminus carries at least residue 84, or residues 84-85 or residues 84-87 of uPAR, demonstrating therefore high discriminating ability among D2D3 fragments. When the data obtained with anti-peptide 3 and anti-uPAR antibodies were divided by one another, the ratio anti-peptide-3/anti-whole uPAR was 0.024 with suPAR and 0.005 with chymotrypsin-cleaved suPAR. However, the ratio was 0.27 with MMP-12-cleaved suPAR (FIG. 16, panel C).

Overall the data demonstrate that the aminoterminal border of the epitope recognized by the anti-Peptide3 antibody is Tyr87 as D2D3 fragments generated by MMP 12 (having Tyr87 as N-terminal aminoacid) are fully recognized, while D2D3 fragment generated by chymotrypsin (having Ser88 as N-terminal aminoacid) are not. This experiment also demonstrates that a simple ELISA can be used to selectively detect specific forms of cleaved uPAR.

REFERENCES QUOTED

Aguirre Ghiso, J. A., Kovalski, K., and Ossowski, L. (1999). Tumor dormancy induced by downregulation of urokinase receptor in human carcinoma involves integrin and MAPK signaling. J Cell Biol 147, 89-104.

B. Degryse, M. R., S. Rabbani, A. Villa, F. Fazioli and Blasi, F. (1999). Src-dependence and pertussis-toxin sensitivity of urokinase receptordependent chemotaxis, and cytoskeleton reorganization in rat smooth muscle cells via the urokinase receptor. Blood 94, 649-662.

Beck, J. M., Preston, A. M., Gyetko, M. R. (1999). Urokinase-type plasminogen activator in inflammatory cell recruitment and host defense against Pneumocystis carinii in mice. Infect. Immun. 67, 879-884.

Behrendt, N., Ploug, M., Patthy, L., Houen, G., Blasi, F. & Danø, K. (1991). The ligand-binding domain of the cell surface receptor for urokinase-type plasminogen activator. J. Biol. Chem. 266, 7842-7847.

Behrendt, N., Jensen, O. N., Engelholm, L. H., Moertz, E., Mann, M. and Dan, K. (2000). A urokinase receptor-associated protein with specific collagen binding properties. J. Biol. Chem. 275, 1993-2002.

Bianchi, E., Ferrero, E., Fazioli, F., Mangili, F., Wang, J., Bender, J. R., Blasi, F., and Pardi, R. (1996). Integrin-dependent induction of functional urokinase receptors in primary T lymphocytes. J Clin Invest 98, 1133-41.

Blasi, F., Fazioli, F., Resnati, M., Sidenius,N. (1997). UPAR mimicking peptide. In WO 98/42733, priority Mar. 20, 1997.

Blasi, F. (1997). uPAR-uPA-PAI-1: a key intersection in proteolysis, adhesion and chemotaxis. Immunol. Today 18, 415-417.

Blasi, F., Conese, M., Møller, L. B., Pedersen, N., Cavallaro, U., Cubellis, M. V., Fazioli; F., Hernandez-Marrero, L., Limongi, P., Muñoz-Canoves, P., Resnati, M., Riittinen, L., Sidenius, N., Soravia, E., Soria, M. R., Stoppelli, M. P., Talarico, D., Teesalu, T., Val (1994). The urokinase receptor: structure, regulation and inhibitor-mediated internalization. Fibrinolysis 8 (Suppl. 1), 182-188.

Borghi, M. O., Panzeri, P., Shattock, R., Sozzani, S., Dobrina, A., and Meroni, P. L. (2000). Interaction between chronically HIV-infected promonocytic cells and human umbilical vein endothelial cells: role of proinflammatory cytokines and chemokines in viral expression modulation. Clin Exp Immunol 120, 93-100.

Boyle, M. D. P., Chiodo, V. A., Lawman, M. J. P., Gee, A. P. and Young, M. (1987). Urokinase: a chemotactic factor for polymorphonuclear leukocytes in vivo. J. Immunol. 139, 169-174.

Braat, E. A., Jie, A. F., Ronday, H. K., Beekman, B., Rijken,, and D. C. (2000). Urokinase-mediated fibrinolysis in the synovial fluid of rheumatoid arthritis patients may be affected by the inactivation of singla chain urokinase type plasminogen activator by thrombin. Ann. Rheum. Dis. 59, 315-318.

Busso N, P. V., Van Ness K, Kolodziesczyk E, Degen J, Bugge T, So A (1998). Exacerbation of antigen-induced arthritis in urokinase-deficient mice. J. Clin. Invest. 102, 41-50.

Butera, S. T., Roberts, B. D., Lam, L., Hodge, T., and Folks, T. M. (1994). Human immunodeficiency virus type 1 RNA expression by four chronically infected cell lines indicates multiple mechanisms of latency. J Virol 68, 2726-30.

Cannon, P., Kim, S. H., Ulich, C., and Kim, S. (1994). Analysis of Tat function in human immunodeficiency virus type 1-infected low-level-expression cell lines U1 and ACH-2. J Virol 68, 1993-7.

Cao, D., Mizukami, I. F., Garni-Wagner, B. A., Kindzelskii, A. L., Todd, R. F., 3rd, Boxer, L. A., and Petty, H. R. (1995). Human urokinase-type plasminogen activator primes neutrophils for superoxide anion release. Possible roles of complement receptor type 3 and calcium. J Immunol 154, 1817-29.

Carmeliet, P., Moons, L., Lijnen, R., Baes, M., Lemaître, V., Tipping, P., Drew, A., Eeckhout, Y., Shapiro, S., Lupu, F. and Collen, D. (1997). Urokinase-generated plasmin activates matrix metalloproteinases during aneurysm formation. Nature Genetics 17, 439-444.

Carmeliet P, Moons L., Dewerchin M, Mackman N, Luther T, Bieier G, Ploplis V, Muller M, Nagy A, Plow E, Gerard R, Edgington T, Risau W, Collen D (1997). Insights in vessel development and vascular disorders using targeted inactivation and transfer of vascular endothelial growth factor, the tissue factor receptor, and the plasminogen system. Ann. N.Y. Acad. Sci. 811, 191-206.

Cerinic, M. M., Generini, S., Partsch, G., Pignone, A., Dini, G., Konttinen, Y. T. and Del Rosso, M. (1998). Synoviocytes from osteoarthritis and rheumatoid arthritis produce plasminogen activators and plasminogen activator inhibitor-1 and display u-PA receptors on their surface. Life Sci. 63, 441-453.

Chapman, H. A. (1997). Plasminogen activators, integrins, and the coordinated regulation of cell adhesion and migration. Curr. Opin. Cell Biol. 9, 714-724.

Chiang, N., Fierro, I. M., Gronert, K. and Serhan, C. N. (2000). Activation of lipoxin A4 receptors by aspitin-triggered lipoxins and select peptides evokes ligand-specific responses in inflammation. J. Exp. Med. 191, 1197-1207.

Coleman J L, G. J., Benach J L (2001). Borrelia burgdorferi and other bacterial products induce expression and release of the urokinase receptor. J. Immunol. 166, 473-480.

Colman, R. W., Pixley, R. A., Najamunnisa, S., Yan, W., Wang, J., Mazar, A., and McCrae, K. R. (1997). Binding of high molecular weight kininogen to human endothelial cells is mediated via a site within domains 2 and 3 of the urokinase receptor. J Clin Invest 100, 1481-7.

Crowley, C. W., Cohen, R. L., Lucas, B. K., Liu, G., Shuman, M. 5A., and Levinson, A. D. (1993). Prevention of metastasis by inhibition of the urokinase receptor. *Proc. Natl. Acad. Sci. USA* 90, 5021-5025.

Dano, K., Behrendt, N., Brunner, N., Ellis, V., Plough, M. and Pyke, C. (1994). The urokinase receptor: protein structure and role in plasminogen activation and cancer invasion. Fibrinolysis 8 (suppl. 1), 189-203.

Dano, K., Blasi, F. et al. (1990). Urokinase-type plasminogen activator receptor. In WO90/12091.

Degryse, B., Resnati, M., Rabbani, S. A., Villa, A., Fazioli, F., & Blasi, F. (1999). Src-dependence and pertussis-toxin sensitivity of urokinase receptor-dependent chemotaxis, and cytoskeleton reorganization in rat smooth muscle cells via the urokinase receptor. Blood 94, 649-662.

Degryse, B., Orlando, S., Resnati, M., Rabbani, S.A. and Blasi, F. (2001). Urokinase/urokinase receptor and vitronectin/avb3 integrin induce chemotaxis and cytoskeleton reorganization through different signaling pathways. Oncogene in press.

Del Rosso, M., Fibbi, G., Matucci Cerinic, M. (1999). The urokinasetype plasminogen activator system and inflammatory joint diseases. Clin. Exper. Rheumatol. 17, 485-498.

Deng, G., Curriden, S. A., Wang, S., Rosenberg, S., and Loskutoff, D. J. (1996). Is plasminogen activator inhibitor-1 the molecular switch that governs urokinase receptor-mediated cell adhesion and release? J Cell Biol 134, 1563-71.

Deng, X., Ueda, H., Su, S. B., Gong, W., Dunlop, N. M., Gao, J. -L;, Murphy, P. M. and Wang, J. M. (1999). A synthetic peptide derived from human immunodeficiency virus type 1 gp120 downregulates the expression and function of chemokine receptors CCR5 and CXCR4 in monocytes by activating the 7-transmembrane G-protein-coupled receptor FPRL1/LXA4R. Blood 94, 1165-1173.

Desreumaux, P., Huet, G., Zerimech, F., Gambiez, L., Balduyck, M. (1999). Acute inflammatory intestinal vascular lesions and in situ abnormalities of the plasminogen activation system in Crohn's disease. Eur. J. Gastroenterol. Hepatol. 11, 1113-1119.

Duh, E. J., Maury, W. J., Folks, T. M., Fauci, A. S., and Rabson, A. B. (1989). Tumor necrosis factor alpha activates human immunodeficiency virus type 1 through induction of nuclear factor binding to the NF-kappa B sites in the long terminal repeat. Proc Natl Acad Sci U S A 86, 5974-8.

Emiliani, S., Van Lint, C., Fischle, W., Paras, P., Jr., Ott, M., Brady, J., and Verdin, E. (1996). A point mutation in the HIV-1 Tat responsive element is associated with postintegration latency. Proc Natl Acad Sci USA 93, 6377-81.

Fazioli, F., Resnati, M, Sidenius, N, Higashimoto, Y, Appella, E and Blasi, F. (1997). The urokinase-sensitive region of the urokinase receptor is responsible for its potent chemotactic activity. *EMBO J.* 16, 7279-7286.

Fazioli, F. a. B., F. (1994). Urokinase-type plasminogen activator and its receptor: new target for anti-metastatic therapy? TiPS 15, 25-29.

Ferrero, E., vettoretto, K., Bondanza, A., Villa, A., Resnati, M., Poggi, A., Zocchi, M. R. (2000). uPA/uPAR system is active in immature dendritic cells derived from CD14+ CD34+ precursors and is down regulated upon matruration. J. Immunol. 164, 712-718.

Fibbi, G., Ziche, M., Morbidelli, L., Magnelli, L. and Del Rosso, M. (1988). Interaction of urokinase with specific receptors stimulates mobilization of bovine adrenal capillary endothelial cells. Exp. Cell Res. 179, 385-395.

Finzi, D., Blankson, J., Siliciano, J. D., Margolick, J. B., Chadwick, K., Pierson, T., Smith, K., Lisziewicz, J., Lori, F., Flexner, C., Quinn, T. C., Chaisson, R. E., Rosenberg, E., Walker, B., Gange, S., Gallant, J., and Siliciano, R. F. (1999). Latent infection of CD4+ T cells provides a mechanism for lifelong persistence of HIV-1, even in patients on effective combination therapy [see comments]. Nat Med 5, 512-7.

Fiore, S. a. S., C. N. (1995). Lipoxin A4 receptor activation is distinct from that of the formyl peptide receptor in myeloid cells: inhibition of CD11/18 expression by lipoxin A4-lipoxin A4 receptor interaction. Biochemistry 34, 16678-16686.

Folks, T. M., Justement, J., Kinter, A., Dinarello, C. A., and Fauci, A. S. (1987). Cytokine-induced expression of HIV-1 in a chronically infected promonocyte cell line. Science 238, 800-2.

Folks, T. M., Justement, J., Kinter, A., Schnittman, S., Orenstein, J., Poli, G., and Fauci, A. S. (1988). Characterization of a promonocyte clone chronically infected with HIV and inducible by 13-phorbol-12-myristate acetate. J Immunol 140, 1117-22.

Franzoso, G., Biswas, P., Poli, G., Carlson, L. M., Brown, K. D., Tomita-Yamaguchi, M., Fauci, A. S., and Siebenlist, U. K. (1994). A family of serine proteases expressed exclusively in myelo-monocytic cells specifically processes the nuclear factor-kappa B subunit p65 in vitro and may impair human immunodeficiency virus replication in these cells. J Exp Med 180, 1445-56.

Gronert, K., Gewirtz, A., Madara, J. L., and Serhan, C. N. (1998). Identification of a human enterocyte Lipoxin A( receptor that is regulated by interleukin (IL)-13 and interferon g and inhibits tumor necrosis factor ainduced IL-8 release. J. Exp. med. 187, 1285-1294.

Gudewicz, P. W. a. B., N. (1987). Human urokinase-type plasminogen activator stimulates chemotaxis of human neutrophils. Biochem. Biophys. Res. Comm., 147, 1176-1181.

Gyetko, M. R., Chen, G. -H., McDonald, R. A., Goodman, R., Huffnagle, G. B., Wilkinson, C. C., Fuller, J. A. and Toews, G. B. (1996). Urokinase is required for the pulmonary inflammatory response to *Cryptococcus neoformans*. A murine transgenic model. J. Clin. Invest. 97, 1818-1826.

Gyetko, M. R., Todd, R. F. 3rd, Wilkinson, C. C., and Sitrin, R. G. (1994). The urokinase receptor is required for human monocyte chemotaxis in vitro. J. Clin. Invest. 93, 1380-1387.

Gyetko, M. R., Sud, S., Kendall, T., Fuller, J. A., Newstead, M. W., Standiford, T. J. (2000). Urokinase receptor-deficient mice have impaired neutrophil recruitment in response to pulmonary *Pseudomonas aeruginosa* infection. J. Immunol. 165, 1513-1519.

Handley, M. A., Steigbigel, R. T. and Morrison, S. A. (1996). A role for urokinase-type plasminogen activator in human immunodeficiency virus type 1 infection of macrophages. J. Virol. 70, 4451-4456.

Hasegawa, T., Sorensen, L., Dohi, M., Rao, N. V., Hoidal, J. R. and Marshall, B. C. (1997). Induction of urokinase-type plasminogen activator receptor by IL-1 beta. Am. J. Respir. Cell Mol. Biol. 16, 683-692.

Higazi, A. A., Upson, R. H., Cohen, R. L., Manuppello, J., Bognacki, J., Henkin, J., McCrae, K. R., Kounnas, M. Z., Strickland, D. K., Preissner, K. T., Lawler, J., and Cines, D. B. (1996). Interaction of single-chain urokinase with its receptor induces the appearance and disappearance of binding epitopes within the resultant complex for other cell surface proteins. Blood 88, 542-51.

Hoyer-Hansen, G., Ploug, M., Behrendt, N., Ronne, E. and Dano, K. (1997). Cell surface acceleration of urokinase-catalyzed receptor cleavage. Eur J Biochem 243, 21-26.

Hoyer-Hansen, G., Behrendt, N., Ploug, M., Dano, K. and Preissner, K. T. (1997). The intact urokinase receptor is required for efficient vitronectin binding: receptor cleavage prevents ligand interaction. FEBS Lett 420, 79-85.

Hoyer-Hansen, G., Ronne, E., Solberg, H., Behrendt, N., Ploug, M., Lund, L. R., Ellis, V. and Dano, K. (1992). Urokinase plasminogen activator cleaves its cell surface receptor releasing the ligand-binding domain. J Biol Chem 267, 18224-18229.

Le, Y., Shen, W., Li, B., Gong, W., Dunlopm, N. M. and Wang, J. M. (1999). A new insight in the role of "old" chemotactic peptide receptor FPR and FPRL1: down-regulation opf chemokine receptors CCR5 and CXCR4. Forum 94, 299-311.

May, A. E., Kanse, S. M., Lund, L. R., Gisler, R. H., Imhof, B. A., and Preissner, K. T. (1998). Urokinase receptor (CD87) regulates leukocyte recruitment via beta 2 integrins in vivo. J Exp Med 188, 1029-37.

Min, H. Y., Doyle, L. V., Vitt, C. R., Zandonella, C. L., Stratton-Thomas, J. R., Shuman, M. A. and Rosenberg, A. (1996). Urokinase receptor antagonists inhibit angiogenesis and primary tumor growth in syngeneic mice. Cancer Res. 56, 2428-2433.

Murphy, P. M. (1996). The N-formyl peptide chemotactic receptors. (Boca Raton, Fla.: CRC Press).

Mustjoki, S., Sidenius, N. Sier, C. F. M. Blasi, F. Elonen, E., Alitalo, R. and Vaheri, A. (2000). Levels of soluble urokinase receptor correlate with number of circulating tumor cells in acute leukemia and decrease rapidly during chemotherapy. Cancer Res. 60, 7126-7132.

Muto, N. F., Martinand-Mari, C., Adelson, M. E., and Suhadolnik, R. J. (1999). Inhibition of replication of reactivated human immunodeficiency virus type 1 (HIV-1) in latently infected U1 cells transduced with an HIV-1 long terminal repeat-driven PKR cDNA construct. J Virol 73, 9021-8.

Nguyen, D. H., Webb, D. J., Catling, A. D., Song, Q., Dhakephalkar, A., Weber, M. J., Ravichandran, K. S. and Gonias, S. L. (2000). Urokinase-type plasminogen activator stimulates the Ras/Extracellular signal-regulated kinase (ERK) signaling pathway andMCF-7 cell migration by a mechanism that requires focal adhesion kinase, Src, and Shc. Rapid dissociation of GRB2/Sps-Shc complex is associated with the transient phosphorylation of ERK in urokinase-treated cells. J. Biol. Chem. 275, 19382-19388.

Nykjaer, A., Christensen, E. I., Vorum, H., Hager, H., Petersen, C. M., Roigaard, H., Min, H. Y., Vilhardt, F., Moller, L. B., Kornfeld, S. and Gliemann, J. (1998). Mannose-6-phosphate/insulin-like growth factor-II receptor targets the urokinase receptor to lysosomes via a novel binding interaction. J. Cell Biol. 141, 815-828.

Nykjaer, A., Møller, B., Todd III, R. F., Christensen, T., Andreasen, P. A., Gliemann, J. and Petersen, C.M. (1994). Urokinase receptor. An activation antigen in human T lymphocytes. *J. Immunol.* 152, 505-516.

Osborn, L., Kunkel, S., and Nabel, G. J. (1989). Tumor necrosis factor alpha and interleukin 1 stimulate the human immunodeficiency virus enhancer by activation of the nuclear factor kappa B. Proc Natl Acad Sci USA 86, 2336-40.

Ossowski, L., Clunie, G., Masucci, M. T. and Blasi, F. (1991). In vivo interaction between urokinase and its receptor: effect on tumor cell invasion. *J. Cell Biol.* 115, 1107-1112.

Ossowski, L.,. (1988). In vivo invasion of modified chorioallantoic membrane by tumor cells: the role of cell surface bound urokinase. *J. Cell Biol.* 107, 2437-2445.

Ossowski, L., Aguirre Ghiso, J. A. (2000). Urokinase receptor and integrin partnership: coordination of signaling for cell adhesion, migration and growth. Curr. Opin. Cell Biol. 12, 613-620.

Pedersen, N., Schmitt, M., Rønne, E., Nicoletti, M. I. Hoyer-Hansen, G., Conese, M., Giavazzi, R., Danø, K., Kuhn, W. Janicke, F. and Blasi, F. (1993). An unoccupied, water soluble urokinase receptor is present in the ascitic fluid and plasma from patients with ovarian cancer. *J. Clin. Invest.* 92, 2160-2167.

Picone, R., Kajtaniak, E. L., Nielsen, L. S., Behrendt, N., Mastronicola, M. R., Cubellis, M. V., Stoppelli, M. P., Pedersen, S., Danø, K. and Blasi, F. (1989). Regulation of urokinase receptors in monocyte-like U937 cells by phorbol esters phorbol myristate acetate. *J. Cell Biol.* 108, 693-702.

Poli, G., Bressler, P., Kinter, A., Duh, E., Timmer, W. C., Rabson, A., Justement, J. S., Stanley, S. and Fauci, A. S. (1990). Interleukin 6 induces human immunodeficiency virus expression in infected monocytic cells alone and in synergy with tumor necrosis factor alpha by transcriptional and post-transcriptional mechanisms. J Exp Med 172, 151-8.

Poli, G., Kinter, A., Justement, J. S., Kehrl, J. H., Bressler, P., Stanley, S., and Fauci, A. S. (1990). Tumor necrosis factor alpha functions in an autocrine manner in the induction of human immunodeficiency virus expression. Proc Natl Acad Sci USA 87, 782-5.

Poli, G., Kinter, A. L., Justement, J. S., Bressler, P., Kehrl, J. H., and Fauci, A. S. (1991). Transforming growth factor beta suppresses human immunodeficiency virus expression and replication in infected cells of the monocyte/macrophage lineage. J Exp Med 173, 589-97.

Pomerantz, R. J., Trono, D., Feinberg, M. B., and Baltimore, D. (1990). Cells nonproductively infected with HIV-1 exhibit an aberrant pattern of viral RNA expression: a molecular model for latency. Cell 61, 1271-6.

Premack, B. A. a. S., T. J. (1996). Chemokine receptors: gateways to inflammation and infection. Nature Med. 2, 1174-1178.

Prickett, K. S., Amberg, D. C. and Hopp, T. P. (1989). A calcium dependent antibody for identification and purification of recombinant proteins. Bio Techniques 7, 580-588.

Prosnitz, E. R., Ye, R. D. (1997). The N-formyl peptide receptor: a model for the study of chemoattractant receptor structure and function. Pharmacol. Ther. 74, 73-102.

Resnati, M., Guttinger, M., Valcamonica, S., Sidenius, N., Blasi, F. and Fazioli, F. (1996). Proteolytic cleavage of the urokinase receptor substitutes for the agonist-induced chemotactic effect. *EMBO J.* 15, 1572-1582.

Rønne, E., Behrendt, N., Ellis, V., Ploug, M., Danø, K. and Høyer-Hansen, G. (1991). Cell induced potentiation of the plasminogen activation system is abolished by a monoclonal antibody that recognizes the N-terminal domain of the urokinase receptor. *FEBS Lett.* 288, 233-236.

Sidenius, N., Olsen, J. E., Sier, C. F. M. Blasi, F., Ullum, H. (2000). Increased plasma levels of soluble urokinase receptor in HIV infected patients are highly correlated with survival. Blood 96, 4091-4095.

Sidenius, N., Nicoletti, I., Mariani, A., Aletti, G., Frigerio, L., Ferrari, A., Agape, V., Stephens, R. W., Frandsen, T. L., Brünner, N., Giavazzi, R., Blasi, F. and Sier, C. F. M. (2001). Presence of domain 1 fragment of urokinase-type plasminogen activator receptor (uPAR) in human body fluids. Submitted.

Sidenius, N., Sier, C F. M. and Blasi, F. (2000). Shedding and cleavage of the urokinase receptor (uPAR): Identification and characterisation of uPAR fragments in vitro and in vivo. FEBS L. 475, 52-56.

Sidenius, N. and Blasi, F. (2000). Domain 1 of the urokinase receptor (uPAR) is required for uPAR-mediated cell binding to vitronectin. FEBS L. 470, 40-46.

Sier, C., Stephens, R, Bizik, J, Mariani, A, Bassan, M, Pedersen, N, Frigerio, L, Ferrari, A, Danø, K, Brünner, N and Blasi, F. (1998). Full-size, GPI-anchor free urokinase receptor is increased in serum of ovarian cancer patients. *Cancer Res.* 58, 1843-1849.

Sier, C. F. M., Sidenius, N., Mariani, A., Aletti, G., Agape, V., Ferrari, A., Stephens, R., Bünner, N., Blasi, F. (1999). Presence of soluble urokinasetype plasminogen activator receptor in urine and possible clinical relevance. *Lab. Invest.* 79, 717-722.

Simon, D. I., Wei, Y., Zhang, L., Rao, N.K., Xu, H., Chen, Z., Liu, Q., Rosenberg, S., Chapman, H. A. (2000). Identification of a urokinase receptorintegrin interaction site. Promiscuous regulator of integrin function. J. Biol. Chem. 275, 10228-10234.

Sitrin, R. G., Pan, P. M., Harper, H. A., Todd, R. F. 3rd, Harsh, D. M., Blackwood, R. A. (2000). Clustering of urokinase receptors (uPAR; CD87) induces proinflammatory signaling in human polymorphonuclear neutrophils. J. Immunol. 165, 3341-3349.

Sitrin, R. G., Pan, P. M., Harper, H. A., Blackwood, R. A., and Todd, R. F., 3rd (1999). Urokinase receptor (CD87) aggregation triggers phosphoinositide hydrolysis and intracellular calcium mobilization in mononuclear phagocytes. J Immunol 163, 6193-200.

Slot, O., Brunner, N. and Stephens, R. W. (2000). Marker of erosive progression in RA. Ann. Rheum. Dis. 59, 656.

Slot, O., Brunner, N., Locht, H., Oxholm, P. and Stephens, R. W. (1999). Soluble urokinase plasminogen activator receptor in plasma of patients with inflammatory rheumatic disorders: increased concentrations in rheumatoid arthritis. Ann. Rheum. Dis. 58, 488-492.

Solberg, H., Rømer, J., Brünner, N., Holm, A., Sidenius, N., Danø, K. and Høyer-Hansen, G. (1994). A cleaved form of the receptor for urokinase-type plasminogen activator in invasive transplanted human and murine tumors. Int J Cancer 58, 877-881.

Speth, C., Pichler, I., Stockl, G., Mair, M., Dierich, M. P. (1998). Urokinase plasminogen activator receptor (uPAR; CD87) expression on monocytic cells and T cells is modulated by HIV-1 infection. Immunobiology 199, 152-162.

Stephens, R. W., Nielsen, H. J., Christensen, I. J., Thorlacius-Ussing, O., Sorensen, S., Dano, K., Brunner, N. (1999). Plasma urokinase receptor levels in patients with colorectal cancer: relationship to prognosis. J. Natl Cancer Inst 91, 869-874.

Stoppelli, M. P., Corti, A., Soffientini, A., Cassani, G., Blasi, F. and Assoian, R.K. (1985). Differentiation-enhanced binding of the amino-terminal fragment of human urokinase plasminogen activator to a specific receptor on U937 monocytes. Proc. Natl. Acad. Sci. USA 82, 4939-4943.

Su, S. B., Gong, W., Gao, J. -L., Shen, W., Murphy, P. M., Oppenheim, J. J. and Wang, J. M. (1999). A seven-transmembrane, G protein coupled receptor, FPRL1, mediates the chemotactic activity of serum amyloid A for human phagocytic cells. J. Exp. Med. 189, 395-402.

Tarui, T., Mazar, A. P., Cines, D. B., Takada, Y. (2000). Urokinase receptor (uPAR/CD87) is a ligand for integrin and mediates cell-cell interaction. J. Biol. Chem. In press, MS. M0082202000, Oct. 26.

Todd, R. F. r., Alvarez, P. A., Brott, D. A. and Liu, D. Y. (1985). Bacterial liposaccharide, phorbol myristate acetate and muramyl dipeptide stimulate the expression of a human monocyte surface antigen Mo3e. J. Immunol. 135,3869.

Vassalli, J. -D., Baccino, D. and Belin, D. (1985). A cellular binding site for the Mr 55,000 form of the human plasminogen activator urokinase. *J. Cell Biol.* 100, 86-92.

Vicenzi, E., Biswas, P., Mengozzi, M., and Poli, G. (1997). Role of pro-inflammatory cytokines and beta-chemokines in controlling HIV replication. J Leukoc Biol 62, 34-40.

Waltz, D. A., and Chapman, H. A. (1994). Reversible cellular adhesion to vitronectin linked to urokinase receptor occupancy. J. Biol. Chem. 269, 14746-14750.

Waltz, D. A., Natkin, L. R., Fujita, R. M., Wei, Y., and Chapman, H. A. (1997). Plasmin and plasminogen activator inhibitor type 1 promote cellular motility by regulating the interaction between the urokinase receptor and vitronectin. J Clin Invest 100, 58-67.

Webb, D. J., Nguyen, D. H., and Gonias, S. L. (2000). Extracellular signal-regulated kinase functions in the urokinase receptor-dependent pathway by which neutralization of low density lipoprotein receptor-related protein promotes fibrosarcoma cell migration and Matrigel invasion. J Cell Sci 113, 123-134.

Wei, Y., Lukashev, M., Simon, D. I., Bodary, S. C., Rosenberg, S., Doyle, M. V., and Chapman, H. A. (1996). Regulation of integrin function by the urokinase receptor. Science 273, 1551-5.

Wei, Y., Yang, X., Liu, Q., Wilkins, J. A., and Chapman, H. A. (1999). A role for caveolin and the urokinase receptor in integrin-mediated adhesion and signaling. J Cell Biol 144, 1285-94.

Xue, W., Kindzelskii, A. L., Todd, R. F., 3rd, and Petty, H. R. (1994). Physical association of complement receptor type 3 and urokinase-type plasminogen activator receptor in neutrophil membranes. J Immunol 152, 4630-40.

Xue, W., Mizukami, I., Todd, R. F., 3rd, and Petty, H. R. (1997). Urokinase-type plasminogen activator receptors associate with beta1 and beta3 integrins of fibrosarcoma cells: dependence on extracellular matrix components. Cancer Res 57, 1682-9.

Yang, X., Chen, Y., and Gabuzda, D. (1999). ERK MAP kinase links cytokine signals to activation of latent HIV-1 infection by stimulating a cooperative interaction of AP-1 and NF-kappaB. J Biol Chem 274, 27981-8.

Yebra, M., Parry, G. C. N., Stromblad, S., Mackman, N., Rosenberg, S., Mueller, B. M., and Cheresh, D. A. (1996). Requirement of receptor-bound urokinase-type plasminogen activator for integrin alphavbeta5-directed cell migration. J Biol Chem 271, 29393-9.

The invention claimed is:

1. Antibody against a uPAR fragment, wherein the uPAR fragment consists only of a member selected from the group consisting of peptides AVTYSRSRYLEC [SEQ ID NO: 1], VTYSRSRYLEC [SEQ ID NO: 5], TYSRSRYLEC [SEQ ID NO: 6], and YSRSRYLEC [SEQ ID NO: 7].

2. Antibody against a uPAR fragment, wherein the uPAR fragment consists only of peptide AVTYSRSRYLEC [SEQ ID NO: 1].

* * * * *